US008956293B2

(12) United States Patent
McCombie et al.

(10) Patent No.: US 8,956,293 B2
(45) Date of Patent: *Feb. 17, 2015

(54) GRAPHICAL 'MAPPING SYSTEM' FOR CONTINUOUSLY MONITORING A PATIENT'S VITAL SIGNS, MOTION, AND LOCATION

(75) Inventors: Devin McCombie, Solana Beach, CA (US); Marshal Dhillon, San Diego, CA (US); Matt Banet, Kihei, HI (US); Gunnar Trommer, Encinitas, CA (US); Jim Moon, Portland, OR (US)

(73) Assignee: Sotera Wireless, Inc., San Diego, CA (US)

( * ) Notice: Subject to any disclaimer, the term of this patent is extended or adjusted under 35 U.S.C. 154(b) by 1285 days.

This patent is subject to a terminal disclaimer.

(21) Appl. No.: 12/469,202

(22) Filed: May 20, 2009

(65) Prior Publication Data
US 2010/0298658 A1 Nov. 25, 2010

(51) Int. Cl.
| | |
|---|---|
| *A61B 5/0205* | (2006.01) |
| *A61B 5/103* | (2006.01) |
| *G08B 19/00* | (2006.01) |
| *A61B 5/00* | (2006.01) |
| *A61B 5/021* | (2006.01) |
| *A61B 5/11* | (2006.01) |
| *G08B 21/04* | (2006.01) |
| *A61B 5/01* | (2006.01) |
| *A61B 5/024* | (2006.01) |
| *A61B 5/0245* | (2006.01) |
| *A61B 5/04* | (2006.01) |
| *A61B 5/0404* | (2006.01) |
| *A61B 5/0452* | (2006.01) |
| *A61B 5/0456* | (2006.01) |
| *A61B 5/08* | (2006.01) |
| *A61B 5/145* | (2006.01) |
| *G06F 19/00* | (2011.01) |

(52) U.S. Cl.
CPC .............. *A61B 5/746* (2013.01); *A61B 5/0205* (2013.01); *A61B 5/02055* (2013.01); *A61B 5/021* (2013.01); *A61B 5/02125* (2013.01); *A61B 5/1117* (2013.01); *A61B 5/1123* (2013.01); *A61B 5/721* (2013.01); *G08B 21/0446* (2013.01); *G08B 21/0453* (2013.01); *A61B 5/0059* (2013.01); *A61B 5/01* (2013.01); *A61B 5/02416* (2013.01); *A61B 5/02438* (2013.01); *A61B 5/0245* (2013.01); *A61B 5/04012* (2013.01); *A61B 5/0404* (2013.01); *A61B 5/0452* (2013.01); *A61B 5/0456* (2013.01); *A61B 5/0816* (2013.01); *A61B 5/11* (2013.01); *A61B 5/1118* (2013.01); *A61B 5/145* (2013.01); *A61B 5/7257* (2013.01); *A61B 2562/0219* (2013.01); *G06F 19/345* (2013.01); *G06F 19/3487* (2013.01)
USPC ............ 600/301; 600/484; 600/595; 340/522

(58) Field of Classification Search
None
See application file for complete search history.

(56) References Cited

U.S. PATENT DOCUMENTS

| | | |
|---|---|---|
| 4,086,916 A | 5/1978 | Freeman et al. |
| 4,263,918 A | 4/1981 | Swearingen et al. |
| 4,270,547 A | 6/1981 | Steffen et al. |
| 4,305,400 A | 12/1981 | Logan |
| 4,577,639 A | 3/1986 | Simon et al. |
| 4,582,068 A | 4/1986 | Phillipps et al. |
| 4,653,498 A | 3/1987 | New, Jr. et al. |
| 4,710,164 A | 12/1987 | Levin et al. |
| 4,722,351 A | 2/1988 | Phillipps et al. |
| 4,802,486 A | 2/1989 | Goodman et al. |
| 4,807,638 A | 2/1989 | Sramek |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,224,928 A | 7/1993 | Sibalis et al. |
| 5,247,931 A | 9/1993 | Norwood |
| 5,289,824 A | 3/1994 | Mills et al. |
| 5,316,008 A | 5/1994 | Suga et al. |
| 5,339,818 A | 8/1994 | Baker et al. |

(Continued)

FOREIGN PATENT DOCUMENTS

| | | |
|---|---|---|
| EP | 0443267 A1 | 8/1991 |
| GB | 2329250 A | 3/1999 |

(Continued)

OTHER PUBLICATIONS

Non-Final Office Action issued by the US Patent and Trademark Office on Jun. 11, 2012 in U.S. Appl. No. 12/469,222.

(Continued)

*Primary Examiner* — H. Sarah Park
(74) *Attorney, Agent, or Firm* — Michael A. Whittaker; Acuity Law Group, P.C.

(57) ABSTRACT

The invention provides a body-worn monitor that measures a patient's vital signs (e.g. blood pressure, SpO2, heart rate, respiratory rate, and temperature) while simultaneously characterizing their activity state (e.g. resting, walking, convulsing, falling). The body-worn monitor processes this information to minimize corruption of the vital signs by motion-related artifacts. A software framework generates alarms/alerts based on threshold values that are either preset or determined in real time. The framework additionally includes a series of 'heuristic' rules that take the patient's activity state and motion into account, and process the vital signs accordingly. These rules, for example, indicate that a walking patient is likely breathing and has a regular heart rate, even if their motion-corrupted vital signs suggest otherwise.

14 Claims, 22 Drawing Sheets

(56) References Cited

U.S. PATENT DOCUMENTS

| | | |
|---|---|---|
| 5,448,991 A | 9/1995 | Polson et al. |
| 5,465,082 A | 11/1995 | Chaco |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,575,284 A | 11/1996 | Athan et al. |
| 5,588,427 A | 12/1996 | Tien |
| 5,593,431 A | 1/1997 | Sheldon |
| 5,632,272 A | 5/1997 | Diab et al. |
| 5,645,060 A | 7/1997 | Yorkey |
| 5,649,543 A | 7/1997 | Hosaka et al. |
| 5,680,870 A | 10/1997 | Hood et al. |
| 5,685,299 A | 11/1997 | Diab et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | DeLorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lichter et al. |
| 6,160,478 A | 12/2000 | Jacobsen et al. |
| 6,168,569 B1 | 1/2001 | McEwen et al. |
| 6,198,394 B1 | 3/2001 | Jacobsen et al. |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 | 7/2001 | Anderson et al. |
| 6,263,222 B1 | 7/2001 | Diab et al. |
| 6,287,262 B1 | 9/2001 | Amano et al. |
| 6,334,065 B1 | 12/2001 | Al-Ali et al. |
| 6,371,921 B1 | 4/2002 | Caro et al. |
| 6,388,240 B2 | 5/2002 | Schulz et al. |
| RE37,852 E | 9/2002 | Aso et al. |
| 6,443,890 B1 | 9/2002 | Schulze et al. |
| 6,480,729 B2 | 11/2002 | Stone |
| 6,491,647 B1 | 12/2002 | Bridger et al. |
| 6,503,206 B1 | 1/2003 | Li et al. |
| 6,516,289 B2 | 2/2003 | David |
| 6,526,310 B1 | 2/2003 | Carter et al. |
| 6,527,729 B1 | 3/2003 | Turcott |
| 6,533,729 B1 | 3/2003 | Khair et al. |
| 6,541,756 B2 | 4/2003 | Schulz et al. |
| 6,544,173 B2 | 4/2003 | West et al. |
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,605,038 B1 | 8/2003 | Teller et al. |
| 6,606,993 B1 | 8/2003 | Wiesmann et al. |
| 6,616,606 B1 | 9/2003 | Petersen et al. |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 | 9/2004 | Mault et al. |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,079,888 B2 | 7/2006 | Oung et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,415 B2 | 1/2008 | Halperin et al. |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | DeLonzor et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |

(56) References Cited

U.S. PATENT DOCUMENTS

| | | |
|---|---|---|
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | DeVaul et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 2001/0004234 A1 | 6/2001 | Petelenz et al. |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1* | 12/2005 | Hwang ........................ 370/310 |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0122469 A1 | 6/2006 | Martel |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0039731 A1 | 2/2008 | McCombie et al. |
| 2008/0077026 A1 | 3/2008 | Banet et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | LeBoeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |

(56) References Cited

U.S. PATENT DOCUMENTS

| | | |
|---|---|---|
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1* | 11/2008 | Tran .............. 600/301 |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | LeBoeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | McCombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| WO | 9932030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008110788 A1 | 9/2008 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Non-Final Office Action issued by the US Patent and Trademark Office on Jun. 8, 2012 in U.S. Appl. No. 12/650,383.
Non-Final Office Action issued by the US Patent and Trademark Office on Jun. 8, 2012 in U.S. Appl. No. 12/650,392.

(56) References Cited

OTHER PUBLICATIONS

Non-Final Office Action issued by the US Patent and Trademark Office on Jun. 20, 2012 in U.S. Appl. No. 12/762,751.
International Search Report and Written Opinion dated Jun. 29, 2012 issued in PCT/US2012/025640.
Non-Final Office Action issued by the US Patent and Trademark Office on Jul. 5, 2012 in U.S. Appl. No. 12/560,138.
"Signal Strength." Oct. 6, 2008. http://web.archive.org/web/20081006200523/http:/!en.wikipedia.org/wiki/Signal_strength.
Non-Final Office Action issued by the US Patent and Trademark Office on May 24, 2012 in U.S. Appl. No. 12/560,111.
Restriction Requirement issued by the US Patent and Trademark Office on Apr. 24, 2012 in U.S. Appl. No. 12/469,107.
Response to Restriction Requirement submitted Jun. 14, 2012 in U.S. Appl. No. 12/469,107.
International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office on May 26, 2011 in U.S. Appl. No. 12/469,151.
Response to Non-Final Office Action submitted Nov. 25, 2011 in U.S. Appl. No. 12/469,151.
Notice of Allowance issued by the US Patent and Trademark Office on Feb. 1, 2012 in U.S. Appl. No. 12/469,151.
Non-Final Office Action issued by the US Patent and Trademark Office on Aug. 4, 2011 in U.S. Appl. No. 12/469,182.
Response to Non-Final Office Action submitted Nov. 25, 2011 in U.S. Appl. No. 12/469,182.
Notice of Allowance issued by the US Patent and Trademark Office on Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office on Apr. 12, 2012 in U.S. Appl. No. 12/559,429.
Non-Final Office Action issued by the US Patent and Trademark Office on Apr. 12, 2012 in U.S. Appl. No. 12/559,430.
Non-Final Office Action issued by the US Patent and Trademark Office on Apr. 24, 2012 in U.S. Appl. No. 12/559,435.
Non-Final Office Action issued by the US Patent and Trademark Office on Apr. 25, 2012 in U.S. Appl. No. 12/762,733.
Non-Final Office Action issued by the US Patent and Trademark Office on Apr. 27, 2012 in U.S. Appl. No. 12/762,822.
Non-Final Office Action issued by the US Patent and Trademark Office on Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
International Search Report and Written Opinion dated Apr. 27, 2012 as reported in PCT/US2011/067441.
Non-Final Office Action issued by the US Patent and Trademark Office on May 7, 2012 in U.S. Appl. No. 12/469,115.
Non-Final Office Action issued by the US Patent and Trademark Office on May 9, 2012 in U.S. Appl. No. 12/762,836.
Non-Final Office Action issued by the US Patent and Trademark Office on May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6) JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.

Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office on May 11, 2012 in U.S. Appl. No. 12/762,846.
Non-Final Office Action issued by the US Patent and Trademark Office on May 11, 2012 in U.S. Appl. No. 12/762,874.
Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Cretikos et al., The Objective Medical Emergency Team Activation Criteria: a case-control study. Resuscitation Apr. 2007;73(1):62-72.
Espina et al., Wireless Body Sensor Network for Continuous Cuffless Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., An improved algorithm for respiration signal extraction from electrocardiogram measured by conductive textile electrodes using instantaneous frequency estimation. Med Bio Eng Comput 2008;46:147-158.
PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.

(56) References Cited

OTHER PUBLICATIONS

Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare . . . Jan. 30-Feb. 1, 2008: 169-172.
Wolf et al., Development of a Fall Detector and Classifier based on a Triaxial Accelerometer Demo Board. 2007:210-213.
Non-Final Office Action issued by the US Patent and Trademark Office on Apr. 30, 2012 in U.S. Appl. No. 12/762,790.
Non-Final Office Action issued by the US Patent and Trademark Office on Mar. 30, 2012 in U.S. Appl. No. 12/469,236.
Non-Final Office Action issued by the US Patent and Trademark Office on Apr. 3, 2012 in U.S. Appl. No. 12/469,094.
Restriction Requirement issued by the US Patent and Trademark Office on Feb. 2, 2012 in U.S. Appl. No. 12/469,222.
Non-Final Office Action issued by the US Patent and Trademark Office on Mar. 27, 2012 in U.S. Appl. No. 12/559,426.
Non-Final Office Action issued by the US Patent and Trademark Office on Apr. 3, 2012 in U.S. Appl. No. 12/559,039.
Non-Final Office Action issued by the US Patent and Trademark Office on Dec. 29, 2011 in U.S. Appl. No. 12/559,080.
Response to Non-Final Office Action submitted Mar. 19, 2012 in U.S. Appl. No. 12/559,080.
Notice of Allowance issued by the US Patent and Trademark Office on Apr. 2, 2012 in U.S. Appl. No. 12/559,080.
Non-Final Office Action issued by the US Patent and Trademark Office on Dec. 15, 2011 in U.S. Appl. No. 12/560,077.
Non-Final Office Action issued by the US Patent and Trademark Office on Mar. 8, 2012 in U.S. Appl. No. 12/560,093.
Restriction Requirement issued by the US Patent and Trademark Office on Dec. 14, 2012 in U.S. Appl. No. 12/560,093.
Response to Restriction Requirement submitted Feb. 15, 2012 in U.S. Appl. No. 12/560,093.
Non-Final Office Action issued by the US Patent and Trademark Office on Mar. 1, 2012 in U.S. Appl. No. 12/560,104.
Restriction Requirement issued by the US Patent and Trademark Office on Jan. 19, 2012 in U.S. Appl. No. 12/469,115.
Response to Restriction Requirement submitted Feb. 15, 2012 in U.S. Appl. No. 12/469,115.
Restriction Requirement issued by the US Patent and Trademark Office on Nov. 14, 2011 in U.S. Appl. No. 12/469,127.
Response to Restriction Requirement submitted Feb. 15, 2012 in U.S. Appl. No. 12/469,127.
Non-Final Office Action issued by the US Patent and Trademark Office on Mar. 9, 2012 in U.S. Appl. No. 12/469,127.
Non-Final Office Action issued by the US Patent and Trademark Office on Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 05, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.
International Search Report and Written Opinion dated Sep. 23, 2010, PCT/US2010/035554.
Non Final Office Action issued by the United States Patent and Trademark Office in 12/559,413 on Nov. 9, 2012.
Response to Office Action issued in 12/762,846 dated Nov. 13, 2012.
Response to Office Action issued in U.S. Appl. No. 12/762,874 dated Nov. 13, 2012.
Response to Office Action issued in U.S. Appl. No. 12/560,111 dated Nov. 26, 2012.
Response to Office Action issued in U.S. Appl. No. 11/930,881 dated Nov. 26, 2012.
Final Rejection issued by the United States Patent and Trademark Office in U.S. Appl. No. 12/559,419 on Nov. 16, 2012.
Non Final Office Action issued by the United States Patent and Trademark Office in U.S. Appl. No. 12/559,408 on Nov. 23, 2012.
Response to Office Action issued in U.S. Appl. No. 12/138,199 dated Nov. 29, 2012.
Response to Office Action issued in U.S. Appl. No. 12/650,383 dated Dec. 7, 2012.
Response to Office Action issued in U.S. Appl. No. 12/650,392 dated Dec. 7, 2012.
Final Rejection issued by the United States Patent and Trademark Office in U.S. Appl. No. 12/559,435 on Dec. 12, 2012.
Final Rejection issued by the United States Patent and Trademark Office in U.S. Appl. No. 12/560,111 on Dec. 12, 2012.
Clifford et al., Measuring Tilt with Low-g Accelerometers. Freescale Semiconductor, Inc., 2005:8 pages.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor for Extreme Environments. Conf Proc IEEE Eng Med Biol Soc. 2004;3:2192-2195.
Thongpithoonrat et al., Networking and Plug-and-Play of Bedside Medical Instruments. Conf Proc IEEE Eng Med Biol Soc. 2008;2008:1514-1517.
Yang et al., Research on Multi-Parameter Physiological Monitor Based on CAN Bus. IFMBE Proceed. 2008;19:417-419.
Zeltwanger, Controller Area Network and CANopen in Medical Equipment. Bus Briefing: Med Dev Manuf Technol. 2002:34-37.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Non Final Office Action issued by the United States Patent and Trademark Office in U.S. Appl. No. 13/432,976 on Dec. 14, 2012.
Final Rejection issued by the United States Patent and Trademark Office in U.S. Appl. No. 12/762,733 on Dec. 20, 2012.
Final Rejection issued by the United States Patent and Trademark Office in U.S. Appl. No. 12/762,846 on Dec. 20, 2012.
Final Rejection issued by the United States Patent and Trademark Office in U.S. Appl. No. 12/650,392 on Jan. 3, 2013.
Final Rejection issued by the United States Patent and Trademark Office in U.S. Appl. No. 12/487,283 on Jan. 3, 2013.
Non Final Office Action issued by the United States Patent and Trademark Office in U.S. Appl. No. 13/292,923 on Jan. 14, 2013.
Notice of Allowance issued by the United States Patent and Trademark Office in U.S. Appl. No. 11/470,708 on Jan. 18, 2013.
International Search Report and Written Opinion issued in PCT/US2012/064302 on Jan. 15, 2013.
Supplemental European Search Report issued in EP 10778376 dated Jan. 31, 2013.
Final Office Action issued by the United States Patent and Trademark Office in U.S. Appl. No. 12/559,039 dated Feb. 11, 2013.
Reddan et al., Intradialytic Blood vol. Monitoring in Ambulatory Hemodialysis Patients: A Randomized Trial. J Am Soc Nephrol. Jul. 2005;16(7):2162-2169.
Final Office Action issued by the United States Patent and Trademark Office in U.S. Appl. No. 12/469,222 dated Feb. 13, 2013.
Non Final Office Action issued by the United States Patent and Trademark Office in U.S. Appl. No. 12/650,383 dated Feb. 15, 2013.
Non Final Office Action issued by the United States Patent and Trademark Office in U.S. Appl. No. 13/346,408 dated Feb. 25, 2013.
Final Office Action issued by the United States Patent and Trademark Office U.S. Appl. No. 12/650,389 dated Mar. 14, 2013.

(56) References Cited

OTHER PUBLICATIONS

Klabunde, Mean Arterial Pressure. Cardiovascular Physiology Concepts. Mar. 8, 2007.http://web.archive.org/web/20070308182914/http://www.cvphysiology.com/Blood%20Pressure/BP006.htm.

Final Office Action issued by the United States Patent and Trademark Office in U.S. Appl. No.12/762,874 dated Mar. 14, 2013.

Non Final Office Action issued by the United States Patent and Trademark Office in U.S. Appl. No. 13/196,326 dated Mar. 22, 2013.

De Scalzi et al., Relationship Between Systolic Time Intervals and Arterial Blood Pressure. Clin Cardiol. 1986;9:545-549.

Ahlstrom et al., Noninvasive investigation of blood pressure changes using the pulse wave transit time: a novel approach in the monitoring of hemodialysis patients. J Artif Organs. 2005;8(3):192-197.

Final Office Action issued by the United States Patent and Trademark Office in U.S. Appl. No. 12/762,751 dated Mar. 29, 2013.

Non-Final Office Action issued by the US Patent and Trademark Office on Jul. 18, 2012 in U.S. Appl. No. 12/650,389.

Chan et al., Noninvasive and Cuffless Measurements of Blood Pressure for Telemedicine. Proceedings of the 23rd Annual International Conference of the IEEE Engineering in Medicine and Biology Society 2001:3 pages.

Fung, Advisory System for Administration of Phenylephrine Following Spinal Anesthesia for Cesarean Section. Master's Thesis. University of British Columbia 2002: 119 pages.

Liu et al., The Changes in Pulse Transit Time at Specific Cuff Pressures during Inflation and Deflation. Proceedings of the 28th IEEE EMBS Annual International Conference New York City, SA, Aug. 30-Sep. 3, 2006:6404-6405.

Nitzan et al., Effects of External Pressure on Arteries Distal to the Cuff During Sphygmomanometry. IEEE Transactions on Biomedical Engineering, Jun. 2005;52(6):1120-1127.

USB 2.0 Specification Engineering Change Notice. Oct. 20, 2000.

Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College,Cambridge, UK, Aug. 19-22, 2007.

Zislin et al., Ways of Improving the Accuracy of Arterial Pressure Oscillometry. Biomedical Engineering 2005;39 (4):174-178.

International Search Report and Written Opinion dated May 29, 2012 issued in PCT/US2012/025648.

Non-Final Office Action issued by the US Patent and Trademark Office on Aug. 3, 2012 in U.S. Appl. No. 12/762,925.

Non-Final Office Action issued by the US Patent and Trademark Office on Aug. 3, 2012 in U.S. Appl. No. 12/762,963.

Non-Final Office Action issued by the US Patent and Trademark Office on Aug. 20, 2012 in U.S. Appl. No. 12/762,777.

Non-Final Office Action issued by the US Patent and Trademark Office on Aug. 21, 2012 in U.S. Appl. No. 12/469,107.

Non-Final Office Action issued by the US Patent and Trademark Office on Aug. 24, 2012 in U.S. Appl. No. 12/762,936.

Non-Final Office Action issued by the US Patent and Trademark Office on Aug. 30, 2012 in U.S. Appl. No. 12/469,202.

Non-Final Office Action issued by the US Patent and Trademark Office on Aug. 31, 2012 in U.S. Appl. No. 12/469,213.

Non-Final Office Action issued by the US Patent and Trademark Office on Sep. 14, 2012 in U.S. Appl. No. 12/650,374.

Drinnan et al., Relation between heart rate and pulse transit time during paced respiration. Physiol. Meas. Aug. 2001;22(3):425-432.

Flash et al., The Coordination of Arm Movements: An Experimentally Confirmed Mathematical Model. J Neurosci. Jul. 1985;5(7):1688-1703.

Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.

Non-Final Office Action issued by the US Patent and Trademark Office on Sep. 17, 2012 in U.S. Appl. No. 12/469,192.

Gallagher, Comparison of Radial and Femoral Arterial Blood Pressure in Children after Cardiopulmonary Bypass. J Clin Monit. Jul. 1985;1(3):168-171.

Park et al., Direct Blood Pressure Measurements in Brachial and Femoral Arteries in Children. Circulation Feb. 1970; 41(2)231-237.

Talkowski, Quantifying Physical Activity in Community Dwelling Older Adults Using Accelerometry. University of Pittsburgh (Dissertation) 2008:1-91.

Non-Final Office Action issued by the US Patent and Trademark Office on Sep. 17, 2012 in U.S. Appl. No. 12/650,354.

Non-Final Office Action issued by the US Patent and Trademark Office on Sep. 21, 2012 in U.S. Appl. No. 12/469,115.

Non-Final Office Action issued by the US Patent and Trademark Office on Sep. 26, 2012 in U.S. Appl. No. 12/560,104.

Packet Definition. The Linux Information Project Jan. 8, 2006 http://www.linfo.org/packet.html.

RS-232. Wikipedia Dec. 5, 2008 http:l/web.archive.org/web/20081205160754/http:/!en.wikipedia.org/wiki/RS-232.

Response to Non-Final Office Action issued in U.S. Appl. No. 12/469,236 dated Sep. 27, 2012.

Response to Non-Final Office Action issued in U.S. Appl. No. 12/487,283 dated Sep. 27, 2012.

Non-Final Office Action issued by the US Patent and Trademark Office on Sep. 28, 2012 in U.S. Appl. No. 12/560,087.

Response to Non-Final Office Action issued in U.S. Appl. No. 12/762,836 dated Oct. 9, 2012.

Non-Final Office Action issued by the US Patent and Trademark Office on Oct. 9, 2012 in U.S. Appl. No. 12/762,726.

Response to Non-Final Office Action issued in U.S. Appl. No. 12/559,429 dated Oct. 12, 2012.

Response to Non-Final Office Action issued in U.S. Appl. No. 12/559,430 dated Oct. 12, 2012.

Final Office Action issued by the US Patent and Trademark Office on Oct. 22, 2012 in U.S. Appl. No. 12/762,822.

Response to Non-Final Office Action issued in U.S. Appl. No. 12/559,435 dated Oct. 23, 2012.

Final Office Action issued by the US Patent and Trademark Office on Oct. 24, 2012 in U.S. Appl. No. 12/599,429.

Final Office Action issued by the US Patent and Trademark Office on Oct. 24, 2012 in U.S. Appl. No. 12/599,430.

Non-Final Office Action issued by the US Patent and Trademark Office on Oct. 23, 2012 in U.S. Appl. No. 12/762,944.

Response to Non-Final Office Action issued in U.S. Appl. No. 12/762,733 dated Oct. 25, 2012.

Final Office Action issued by the US Patent and Trademark Office on Oct. 25, 2012 in U.S. Appl. No. 12/599,426.

Alves et al., CAN Protocol: A Laboratory Prototype for Fieldbus Applications. XIX IMEKO World Congress Fundamental and Applied Metrology Sep. 6-11, 2009 Lisbon, Portugal. 4 pages :454-457 ISBN 978-963-88410-0-1.

Benefits of Digital Sensors. Gems Sensors. Feb. 14, 2008 http://web.archive.org/web/20080214122230/http://www.sensorland.com/HowPage054.html.

Final Office Action issued by the US Patent and Trademark Office on Oct. 25, 2012 in U.S. Appl. No. 12/762,790.

Final Office Action issued by the US Patent and Trademark Office on Oct. 26, 2012 in U.S. Appl. No. 12/762,836.

Non-Final Office Action issued by the US Patent and Trademark Office on Oct. 30, 2012 in U.S. Appl. No. 12/559,386.

Non-Final Office Action issued by the US Patent and Trademark Office on Nov. 6, 2012 in U.S. Appl. No. 12/559,379.

Non-Final Office Action issued by the US Patent and Trademark Office on Nov. 6, 2012 in U.S. Appl. No. 12/650,370.

Poon and Zhang, Cuff-Less and Noninvasive Measurements of Arterial Blood Pressure by Pulse Transit Time. Conf Proc IEEE Eng Med Biol Soc. 2005;6:5877-5880.

Non-Final Office Action issued by the US Patent and Trademark Office on Nov. 7, 2012 in U.S. Appl. No. 12/559,392.

Non-Final Office Action issued by the US Patent and Trademark Office on Oct. 24, 2012 in U.S. Appl. No. 12/559,403.

\* cited by examiner

GRAPHICAL 'MAPPING SYSTEM' FOR CONTINUOUSLY MONITORING A PATIENT'S VITAL SIGNS, MOTION, AND LOCATION

CROSS REFERENCES TO RELATED APPLICATION

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to medical devices for monitoring vital signs, e.g., arterial blood pressure.

2. Description of the Related Art

False alarms generated by conventional vital sign monitors can represent up to 90% of all alarms in critical and perioperative care, and are therefore a source of concern. A variety of factors cause false alarms, one of which is motion-related artifacts. Ultimately false alarms can have a severe impact on the safety of hospitalized patients: they can desensitize medical professionals toward 'true positive' alarms, lead them to set dangerously wide alarm thresholds, or even drive them to completely disable alarms. This can have a particularly profound impact in lower-acuity areas of the hospital, i.e. areas outside the intensive care unit (ICU), emergency department (ED), or operating room (OR), where the ratio of medical professionals to patients can be relatively low. In these areas a single medical professional (e.g. a nurse) often has to care for a large number of patients, and necessarily relies on automated alarms operating on vital sign monitors to effectively monitor their patients.

Studies in critical care environments indicate that the majority of false positive alarms are simple 'threshold alarms', meaning they are generated when a patient's vital sign exceeds a predetermined threshold. Patient motion can result in a vital sign having an erroneous high or low value, which in turn can trigger the false alarm. In most cases, these alarms lack any real clinical meaning, and go away after about 20 seconds when they are not acknowledged. Alarms can also be artificially induced when a patient is moved or manipulated, or if there is an actual problem with the vital sign monitor. False alarms due to motion-related artifacts are particularly very high when measured from ambulatory patients.

Blood pressure is a vital sign that is particularly susceptible to false alarms. In critical care environments like the ICU and OR, blood pressure can be continuously monitored with an arterial catheter inserted in the patient's radial or femoral artery. Alternatively, blood pressure can be measured intermittently using a pressured cuff and a technique called oscillometry. A vital sign monitor performs both the catheter and cuff-based measurements of blood pressure. Alternatively, blood pressure can be monitored continuously with a technique called pulse transit time (PTT), defined as the transit time for a pressure pulse launched by a heartbeat in a patient's arterial system. PTT has been shown in a number of studies to correlate to systolic (SYS), diastolic (DIA), and mean (MAP) blood pressures. In these studies, PTT is typically measured with a conventional vital signs monitor that includes separate modules to determine both an electrocardiogram (ECG) and pulse oximetry (SpO2). During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that attaches to a patient's finger, and includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation detected by the photodetector to determine the patient's blood oxygen saturation level and a time-dependent waveform called a photoplethysmograph ('PPG'). Time-dependent features of the PPG indicate both pulse rate and a volumetric absorbance change in an underlying artery caused by the propagating pressure pulse.

Typical PTT measurements determine the time separating a maximum point on the QRS complex (indicating the peak of ventricular depolarization) and a foot of the optical waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff and oscillometry. Typically during the calibration process the blood pressure cuff is applied to the patient, used to make one or more blood pressure measurements, and then left on the patient. Going forward, the calibration blood pressure measurements are used, along with a change in PTT, to continuously measure the patient's blood pressure (defined herein as 'cNIBP). PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and PPG, which are then processed to determine PTT. U.S. Pat. No. 5,964,701 describes a finger-ring sensor that includes an optical system for detecting a PPG, and an accelerometer for detecting motion.

SUMMARY OF THE INVENTION

To improve the safety of hospitalized patients, particularly those in lower-acuity areas, it is desirable to have a vital sign monitor operating algorithms featuring: 1) a low percentage of false positive alarms/alerts; and 2) a high percentage of true positive alarms/alerts. The term 'alarm/alert', as used herein, refers to an audio and/or visual alarm generated directly by a monitor worn on the patient's body, or alternatively a remote monitor (e.g., a central nursing station). To accomplish this, the invention provides a body-worn monitor that measures a patient's vital signs (e.g. SYS, DIA, SpO2, heart rate, respiratory rate, and temperature) while simultaneously characterizing their activity state (e.g. resting, walking, convulsing, falling). The body-worn monitor processes this information to minimize corruption of the vital signs by motion-related artifacts. A software framework generates alarms/alerts based on threshold values that are either preset or determined in real time. The framework additionally includes a series of 'heuristic' rules that take the patient's activity state and motion into account, and process the vital signs accordingly. These rules, for example, indicate that a walking patient is likely breathing and has a regular heart rate, even if their motion-corrupted vital signs suggest otherwise.

The body-worn monitor features a series of sensors that measure time-dependent PPG, ECG, motion (ACC), and pressure waveforms to continuously monitor a patient's vital signs, degree of motion, posture and activity level. Blood pressure, a vital sign that is particularly useful for characterizing a patient's condition, is typically calculated from a PTT value determined from the PPG and ECG waveforms. Once determined, blood pressure and other vital signs can be further processed, typically with a server within a hospital, to alert a medical professional if the patient begins to decompensate.

In other embodiments, PTT can be calculated from time-dependent waveforms other than the ECG and PPG, and then processed to determine blood pressure. In general, PTT can be calculated by measuring a temporal separation between features in two or more time-dependent waveforms measured from the human body. For example, PTT can be calculated from two separate PPGs measured by different optical sensors disposed on the patient's fingers, wrist, arm, chest, or virtually any other location where an optical signal can be measured using a transmission or reflection-mode optical configuration. In other embodiments, PTT can be calculated using at least one time-dependent waveform measured with an acoustic sensor, typically disposed on the patient's chest. Or it can be calculated using at least one time-dependent waveform measured using a pressure sensor, typically disposed on the patient's bicep, wrist, or finger. The pressure sensor can include, for example, a pressure transducer, piezoelectric sensor, actuator, polymer material, or inflatable cuff.

In one aspect, the invention provides a system for processing at least one vital sign from a patient along with a motion parameter and, in response, generating an alarm. The system features two sensors to measure the vital sign, each with a detector configured to detect a time-dependent physiological waveform indicative of one or more contractile properties of the patient's heart. The contractile property, for example, can be a beat, expansion, contraction, or any time-dependent variation of the heart that launches both electrical signals and a bolus of blood. The physiological waveform, for example, can be an ECG waveform measured from any vector on the patient, a PPG waveform, an acoustic waveform measured with a microphone, or a pressure waveform measured with a transducer. In general, these waveforms can be measured from any location on the patient. The system includes at least two motion-detecting sensors (e.g. analog or digital accelerometers) positioned on locations selected from a forearm, upper arm, and a body location other than the forearm or upper arm of the patient. Here, 'forearm' means any portion of the arm below the elbow, e.g. the forearm, wrist, hand, and fingers. 'Upper arm' means any portion of the arm above and including the elbow, e.g. the bicep, shoulder, and armpit. Each of the motion-detecting sensors generate at least one motion waveform, and typically a set of three motion waveforms (each corresponding to a different axis), indicative of motion of the location on the patient's body to which it is affixed.

A processing component (e.g., an algorithm or any computation function operating on a microprocessor or similar logic device in the wrist-worn transceiver) receives and processes the time-dependent physiological and motion waveforms. The processing component performs the following steps: (i) calculates at least one vital sign (e.g., SYS, DIA, SpO2, heart rate, and respiratory rate) from the first and second time-dependent physiological waveforms; and (ii) calculates at least one motion parameter (e.g. posture, activity state, arm height, and degree of motion) from the motion waveforms. A second processing component, which can be another algorithm or computational function operating on the microprocessor, receives the vital sign and motion parameter and determines: (i) a first alarm condition, calculated by comparing the vital sign to an alarm threshold; (ii) a second alarm condition, calculated from the motion parameter; and (iii) an alarm rule, determined by collectively processing the first and second alarm conditions with an alarm algorithm. The alarm rule indicates, e.g., whether or not the system generates an alarm.

In embodiments, the motion parameter corresponds to one of the following activities or postures: resting, moving, sitting, standing, walking, running, falling, lying down, and convulsing. Typically the alarm rule automatically generates the alarm if the motion parameter is one of falling or convulsing, as these activities typically require immediate medical attention. If the motion parameter corresponds to walking or most ambulatory motions, then the alarm rule does not necessarily generate an alarm for vital signs such as heart rate, respiratory rate, and SpO2. Here, the patient is assumed to be in a relatively safe state since they are walking. However, even while the patient is in this activity state, the alarm rule can still generate an alarm if the heart rate exceeds an alarm threshold that is increased relative to its initial value. If the motion parameter corresponds to standing, and the vital sign is blood pressure, then the alarm rule can generate the alarm if the blood pressure exceeds an alarm threshold that is decreased relative to its initial value. This is because it is relatively normal for a patient's blood pressure to safely drop as the move from a sitting or lying posture to a standing posture.

In embodiments, the vital sign is blood pressure determined from a time difference (e.g. a PTT value) between features in the ECG and PPG waveforms, or alternatively using features between any combination of time-dependent ECG, PPG, acoustic, or pressure waveforms. This includes, for example, two PPG waveforms measured from different locations on the patient's body. The motion parameter can be calculated by processing either a time or frequency-dependent component from at least one motion waveform. For example, the processing component can determine that the patient is walking, convulsing, or falling by: i) calculating a frequency-dependent motion waveform (e.g. a power spectrum of a time-dependent motion waveform); and ii) analyzing a band of frequency components from the frequency-dependent waveform. A band of frequency components between 0-3 Hz typically indicates that the patient is walking, while a similar band between 0-10 Hz typically indicates that the patient is convulsing. Finally, a higher-frequency band between 0-15 Hz typically indicates that a patient is falling. In this last case, the time-dependent motion waveform typically includes a signature (e.g. a rapid change in value) that can be further processed to indicate falling. Typically this change represents at least a 50% change in the motion waveform's value within a time period of less than 2 seconds. In other embodiments, the first processing component determines the motion parameter by comparing a parameter determined from the motion waveform (e.g., from a time or frequency-dependent parameter of the waveform) to a pre-determined ROC threshold value associated with a pre-determined ROC curve.

In embodiments, both the first and second processing components are algorithms or computational functions operating on one or more microprocessors. Typically the processing components are algorithms operating on a common microprocessor worn on the patient's body. Alternatively, the first processing component is an algorithm operating on a processor worn on the patient's body, and the second processing component is an algorithm operating on a remote computer (located, e.g., at a central nursing station).

In another aspect, the invention provides a method for continuously monitoring a patient featuring the following steps: (i) detecting first and second time-dependent physiological waveforms indicative of one or more contractile properties of the patient's heart with first and second body-worn sensors; (ii) detecting sets of time-dependent motion waveforms with at least two body-worn, motion-detecting sensors; (iii) processing the first and second time-dependent physiological waveforms to determine at least one vital sign from the patient; (iv) analyzing a portion of the sets of time-dependent motion waveforms with a motion-determining algorithm to determine the patient's activity state (e.g. resting, moving, sitting, standing, walking, running, falling, lying down, and convulsing); and (v) generating an alarm by processing the patient's activity state and comparing the vital sign to a predetermined alarm criteria corresponding to this state.

In embodiments, the analyzing step features calculating a mathematical transform (e.g. a Fourier Transform) of at least one time-dependent motion waveform to determine a frequency-dependent motion waveform (e.g. a power spectrum), and then analyzing frequency bands in this waveform to determine if the patient is walking, convulsing, or falling. This step can also include calculating a time-dependent change or variation in the time-dependent waveforms, e.g. a standard deviation, mathematical derivative, or a related statistical parameter. In other embodiments, the analyzing step includes determining the motion parameter by comparing a time-dependent motion waveform to a mathematical function using, e.g., a numerical fitting algorithm such as a linear least squares or Marquardt-Levenberg non-linear fitting algorithm.

The analyzing step can include calculating a 'logit variable' from at least one time-dependent motion waveform, or a waveform calculated therefrom, and comparing the logit variable to a predetermined ROC curve to determine the patient's activity state. For example, the logit variable can be calculated from at least one time or frequency-dependent motion waveform, or a waveform calculated therefrom, and then compared to different ROC curves corresponding to various activity and posture states.

In another aspect, the invention provides a system for continuously monitoring a group of patients, wherein each patient in the group wears a body-worn monitor similar to those described herein. Additionally, each body-worn monitor is augmented with a location sensor. The location sensor includes a wireless component and a location processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the user interface is a graphical user interface featuring a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11, 802.15.4, or cellular protocols. In this case a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS).

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associate with the medical professional features a display wherein the user can select to display information (e.g. vital signs, location, and alarms) corresponding to a particular patient. This monitor can also include a voice interface so the medical professional can communicate with the patient.

In another aspect, the invention provides a body-worn monitor featuring optical sensor that measures two time-dependent optical waveforms (e.g. PPG waveforms) from the patient's body, and an electrical sensor featuring at least two electrodes and an electrical circuit that collectively measure a first time-dependent electrical waveform (e.g., an ECG waveform) indicating the patient's heart rate, and a second time-dependent electrical waveform (e.g. a waveform detected with impedance pneumography) indicating the patient's respiratory rate. The monitor includes at least two motion-detecting sensors positioned on two separate locations on the patient's body. A processing component, similar to that described above, determines: (i) a time difference between features in one of the time-dependent optical and electrical waveforms; (ii) a blood pressure value calculated from the time difference; iii) an SpO2 value calculated from both the first and second optical waveforms; (iii) a heart rate calculated from one of the time-dependent electrical waveforms; (iv) a respiratory rate calculated from the second time-dependent electrical waveform; (v) at least one motion parameter calculated from at least one motion waveform; and (vi) an alarm parameter calculated from at least one of the blood pressure value, SpO2 value, heart rate, respiratory rate, and the motion parameter.

In embodiments, the processing component renders numerical values corresponding to the blood pressure value, SpO2 value, heart rate, and respiratory rate on a graphical display. These parameters, however, are not rendered when the motion parameter corresponds to a moving patient (e.g. a walking patient). Using the motion waveforms, the monitor can detect when the patient is lying down, and from the electrical waveforms if their respiratory rate has ceased for an extended period of time (e.g. at least 20 seconds). In this case, for example, the processing component can generate an alarm parameter corresponding to apnea. The time-dependent electrical waveforms can be further processed to determine heart rate along with an additional parameter, such as VFIB, VTAC, and ASY, defined in detail below. Similarly, the processing component can analyze the time-dependent optical waveforms to determine a pulse rate, and can determine a pulse pressure from a difference between diastolic and systolic blood pressures. It determines a 'significant pulse rate' if the pulse rate is greater than 30 beats per minute, and the pulse pressure is greater than 10 mmHg. The monitor then generates an alarm parameter corresponding to one of VFIB, VTAC, and ASY if these parameters are determined from the patient and a significant pulse rate is not present.

In other embodiments, the processing component can process at least one motion waveform to determine a number of times the patient moves from lying in a first position to lying in a different position, and generate an alarm parameter if the number is less than a threshold value (e.g. once per four hours). Such an alarm indicates, for example, a 'bed sore index', i.e. an index that indicates when the patient may develop lesions due to inactivity. The monitor can also include a temperature sensor, configured, e.g., to attach to a portion of the patient's chest.

In another aspect, the invention provides a body-worn monitor described above for monitoring a patient's vital signs using time-dependent ECG and PPG waveforms. The processing component determines at least one motion parameter measured by a motion-detecting sensor (e.g. an accelerometer) representing the patient's posture, activity state, and degree of motion. The motion parameter is calculated by comparing a component determined from a time or frequency-dependent waveform or a ROC curve to a predetermined threshold value. An alarm is generated by collectively processing a vital sign and the motion parameter with an alarm algorithm. The monitor can include a graphical display, worn on the patient's body, which renders numerical values indicating the patient's vital signs, and iconic images indicating both the motion parameter and the alarm. The graphical display typically includes a first user interface for a patient, and a second user interface for a medical professional that is rendered after the processing unit processes an identifier (e.g. a barcode or radio frequency identification, or RFID) corresponding to the medical professional. The body-worn monitor can also include a wireless transceiver that transmits the vital sign, motion parameter, and alarm to a remote computer which further includes a graphical display for rendering this information.

In another aspect, the invention provides a method for generating an alarm while monitoring vital signs and posture of a patient. A monitor, similar to that described above, measures vital signs from time-dependent waveforms (e.g. any combination of optical, electrical, acoustic, or pressure waveforms) and a patient's posture with at least one motion-detecting sensor positioned on the patient's torso (e.g., an accelerometer positioned on the patient's chest). The processing component analyzes at least a portion of a set of time-dependent motion waveforms generated by the motion-detecting sensor to determine a vector corresponding to motion of the patient's torso. It then compares the vector to a coordinate space representative of how the motion-detecting sensor is oriented on the patient to determine a posture parameter, which it then processes along with the vital sign to generate an alarm. The alarm, for example, is indicated by a variance of the vital sign relative to a predetermined alarm criterion, and is regulated according to the patient's posture.

In embodiments, the method generates the alarm in response to a change in the patient's posture, e.g. if the patient is standing up, or if their posture changes from lying down to either sitting or standing up, or from standing up to either sitting or lying down.

To determine the vector the method includes an algorithm or computation function that analyzes three time-dependent motion waveforms, each corresponding to a unique axis of the motion-detecting sensor. The motion waveforms can yield three positional vectors that define a coordinate space. In a preferred embodiment, for example, the first positional vector corresponds to a vertical axis, a second positional vector corresponds to a horizontal axis, and the third positional vector corresponds to a normal axis extending normal from the patient's chest. Typically the posture parameter is an angle, e.g. an angle between the vector and at least one of the three positional vectors. For example, the angle can be between the vector and a vector corresponding to a vertical axis. The patient's posture is estimated to be upright if the angle is less than a threshold value that is substantially equivalent to 45 degrees (e.g., 45 degrees+/−10 degrees); otherwise, the patient's posture is estimated to be lying down. If the patient is lying down, the method can analyze the angle between the vector and a vector corresponding to a normal axis extending normal from the patient's chest. In this case, the patient's posture is estimated to be supine if the angle is less than a threshold value substantially equivalent to 35 degrees (e.g., 35 degrees+/−10 degrees), and prone if the angle is greater than a threshold value substantially equivalent to 135 degrees (e.g., 135 degrees+/−10 degrees). Finally, if the patient is lying down, the method can analyze the angle between the vector and a vector corresponding to a horizontal axis. In this case, the patient is estimated to be lying on a first side if the angle is less than a threshold value substantially equivalent to 90 degrees (e.g., 90 degrees+/−10 degrees), and lying on an opposing side if the angle is greater than a threshold value substantially equivalent to 90 degrees (e.g., 90 degrees+/−10 degrees).

Blood pressure is determined continuously and non-invasively using a technique, based on PTT, which does not require any source for external calibration. This technique, referred to herein as the 'composite technique', operates on the body-worn monitor and wirelessly transmits information describing blood pressure and other vital signs to the remote monitor. The composite technique is described in detail in the co-pending patent application entitled: VITAL SIGN M FOR MEASURING BLOOD PRESSURE USING OPTICAL, ELECTRICAL, AND PRESSURE WAVEFORMS (U.S. Ser. No. 12/138, 194; filed Jun. 12, 2008), the contents of which are fully incorporated herein by reference.

Still other embodiments are found in the following detailed description of the invention, and in the claims.

DETAILED DESCRIPTION OF THE INVENTION

System Overview

Figure 1:
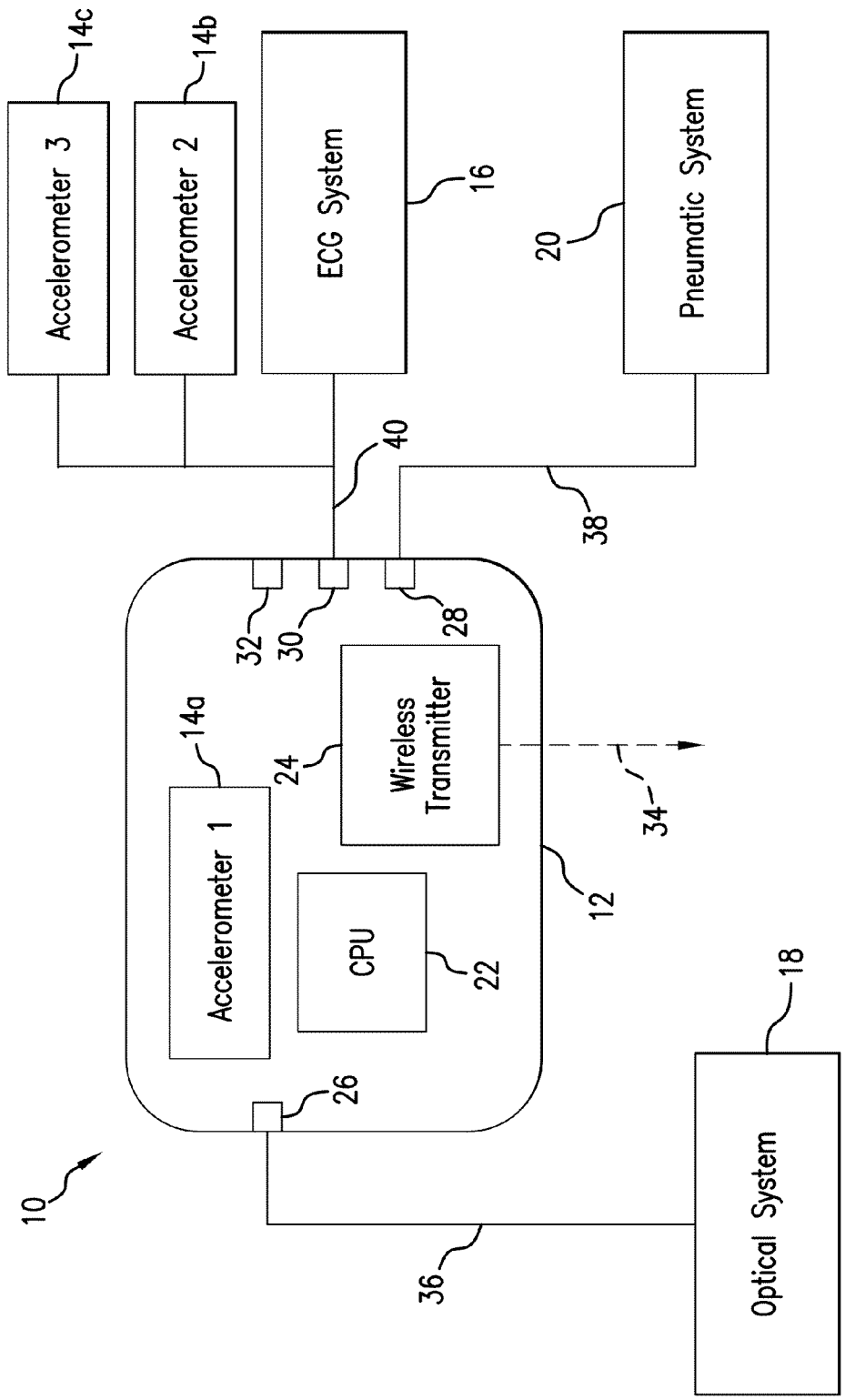
FIG. 1 shows a schematic drawing of a body-worn monitor featuring three accelerometers for detecting motion, along with ECG, optical, and pneumatic systems for measuring vital signs.

FIG. 1 shows a schematic drawing of a body-worn monitor 10 according to the invention featuring a wrist-worn transceiver 12 that continuously determines vital signs (e.g. SYS, DIA, SpO2, heart rate, respiratory rate, and temperature) and motion (e.g. posture, arm height, activity level, and degree of motion) for, e.g., an ambulatory patient in a hospital. The monitor 10 is coupled to a software framework for determining alarms/alerts that processes both the motion and vital sign information with algorithms that reduce the occurrence of false alarms in, e.g., a hospital. The transceiver 12 connects to three separate accelerometers 14a, 14b, 14c distributed along a patient's arm and torso and connected to a single cable. Each of these sensors measures three unique ACC waveforms, each corresponding to a separate axis (x, y, or z), which are digitized internally and sent to a computer processing unit (CPU) 22 within the transceiver 12 for processing. The transceiver 12 also connects to an ECG system 16 that measures an ECG waveform, an optical system 18 that measures a PPG waveform, and a pneumatic system 20 for making cuff-based 'indexing' blood pressure measurements according to the composite technique. Collectively, these systems 14a-c, 16, 18, and 20 continuously measure the patient's vital signs and motion, and supply information to the software framework that calculates alarms/alerts.

The ECG 16 and pneumatic 20 systems are stand-alone systems that include a separate microprocessor and analog-to-digital converter. During a measurement, they connect to the transceiver 12 through connectors 28, 30 and supply digital inputs using a communication protocol that runs on a controller-area network (CAN) bus. The CAN bus is a serial interface, typically used in the automotive industry, which allows different electronic systems to effectively communicate with each other, even in the presence of electrically noisy environments. A third connector 32 also supports the CAN bus and is used for ancillary medical devices (e.g. a glucometer) that is either worn by the patient or present in their hospital room.

The optical system 18 features an LED and photodetector and, unlike the ECG 16 and pneumatic 20 systems, generates an analog electrical signal that connects through a cable 36 and connector 26 to the transceiver 12. As is described in detail below, the optical 18 and ECG 16 systems generate synchronized time-dependent waveforms that are processed with the composite technique to determine a PTT-based blood pressure along with motion information.

The first accelerometer 14a is surface-mounted on a printed circuited board within the transceiver 12, which is typically worn on the patient's wrist like a watch. The second 14b accelerometer is typically disposed on the upper portion of the patient's arm and attaches to a cable 40 that connects the ECG system 16 to the transceiver 12. The third accelerometer 14c is typically worn on the patient's chest proximal to the ECG system 16. The second 14b and third 14c accelerometers integrate with the ECG system 16 into a single cable 40, as is described in more detail below, which extends from the patient's wrist to their chest and supplies digitized signals over the CAN bus. In total, the cable 40 connects to the ECG system 16, two accelerometers 14b, 14c, and at least three ECG electrodes (shown in FIGS. 20A and 20B, and described in more detail below). The cable typically includes 5 separate wires bundled together with a single protective cladding: the wires supply power and ground to the ECG system 16 and accelerometers 14b, 14c, provide high signal and low signal transmission lines for data transmitted over the CAN protocol, and provide a grounded electrical shield for each of these four wires. It is held in place by the ECG electrodes, which are typically disposable and feature an adhesive backing, and a series of bandaid-like disposable adhesive strips. This simplifies application of the system and reduces the number of sensing components attached to the patient.

To determine posture, arm height, activity level, and degree of motion, the transceiver's CPU 22 processes signals from each accelerometer 14a-c with a series of algorithms, described in detail below. In total, the CPU can process nine unique, time-dependent signals ($ACC_{1-9}$) corresponding to the three axes measured by the three separate accelerometers. Specifically, the algorithms determine parameters such as the patient's posture (e.g., sitting, standing, walking, resting, convulsing, falling), the degree of motion, the specific orientation of the patient's arm and how this affects vital signs (particularly blood pressure), and whether or not time-dependent signals measured by the ECG 16, optical 18, or pneumatic 20 systems are corrupted by motion. Once this is complete, the transceiver 12 uses an internal wireless transmitter 24 to send information in a series of packets, as indicated by arrow 34, to a remote monitor within a hospital. The wireless transmitter 24 typically operates on a protocol based on 802.11 and communicates with an existing network within the hospital. This information alerts a medical professional, such as a nurse or doctor, if the patient begins to decompensate. A server connected to the hospital network typically generates this alarm/alert once it receives the patient's vital signs, motion parameters, ECG, PPG, and ACC waveforms, and information describing their posture, and compares these parameters to preprogrammed threshold values. As described in detail below, this information, particularly vital signs and motion parameters, is closely coupled together. Alarm conditions corresponding to mobile and stationary patients are typically different, as motion can corrupt the accuracy of vital signs (e.g., by adding noise), and induce changes in them (e.g., through acceleration of the patient's heart and respiratory rates).

General Methodology for Alarms/Alerts

Algorithms operating on either the body-worn monitor or remote monitor generate alarms/alerts that are typically grouped into three general categories: 1) motion-related alarms/alerts indicating the patient is experiencing a traumatic activity, e.g. falling or convulsing; 2) life-threatening alarms/alerts typically related to severe events associated with a patient's cardiovascular or respiratory systems, e.g. asystole (ASY), ventricular fibrillation (VFIB), ventricular tachycardia (VTAC), and apnea (APNEA); and 3) threshold alarms/alerts generated when one of the patient's vital signs (SYS, DIA, SpO2, heart rate, respiratory rate, or temperature) exceeds a threshold that is either predetermined or calculated directly from the patient's vital signs. The general methodology for generating alarms/alerts in each of these categories is described in more detail below.

Motion-Related Alarms/Alerts

Figure 3:
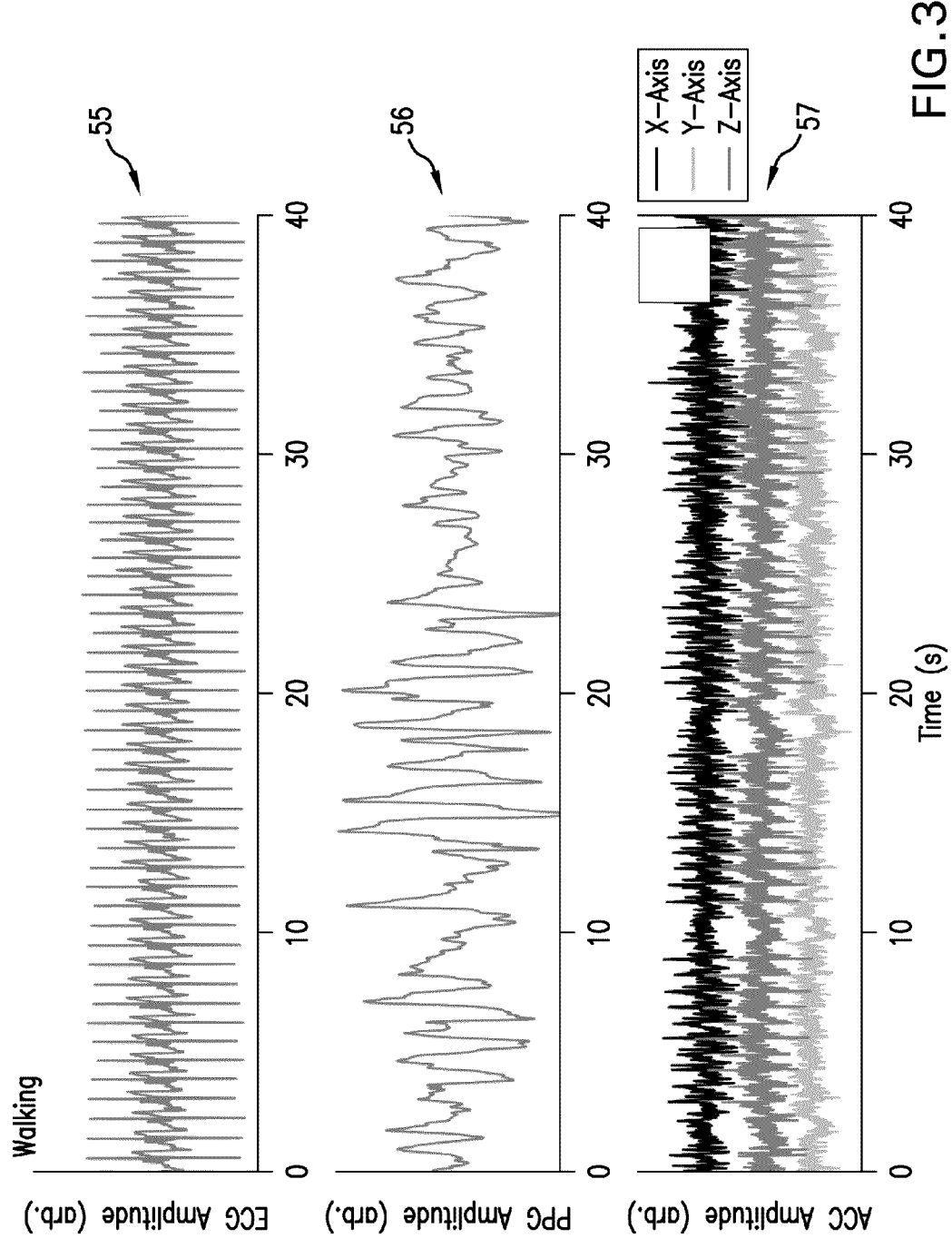
FIG. 3 shows a graph of time-dependent waveforms (ECG, PPG, and ACC) generated from a walking patient by, respectively, the ECG system, the optical system, and the accelerometer system of FIG. 1.
Figure 4:
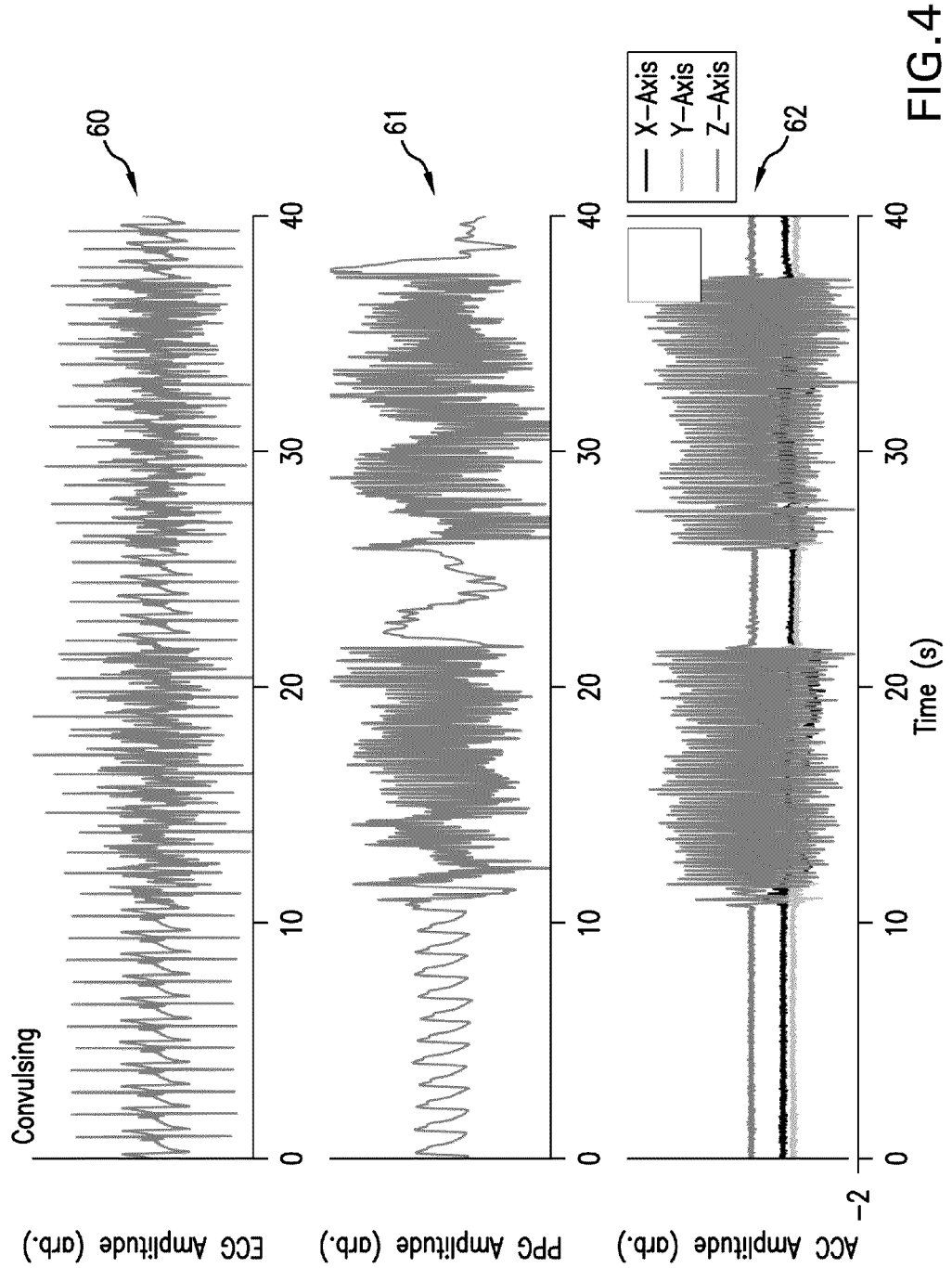
FIG. 4 shows a graph of time-dependent waveforms (ECG, PPG, and ACC) generated from a convulsing patient by, respectively, the ECG system, the optical system, and the accelerometer system of FIG. 1.
Figure 5:
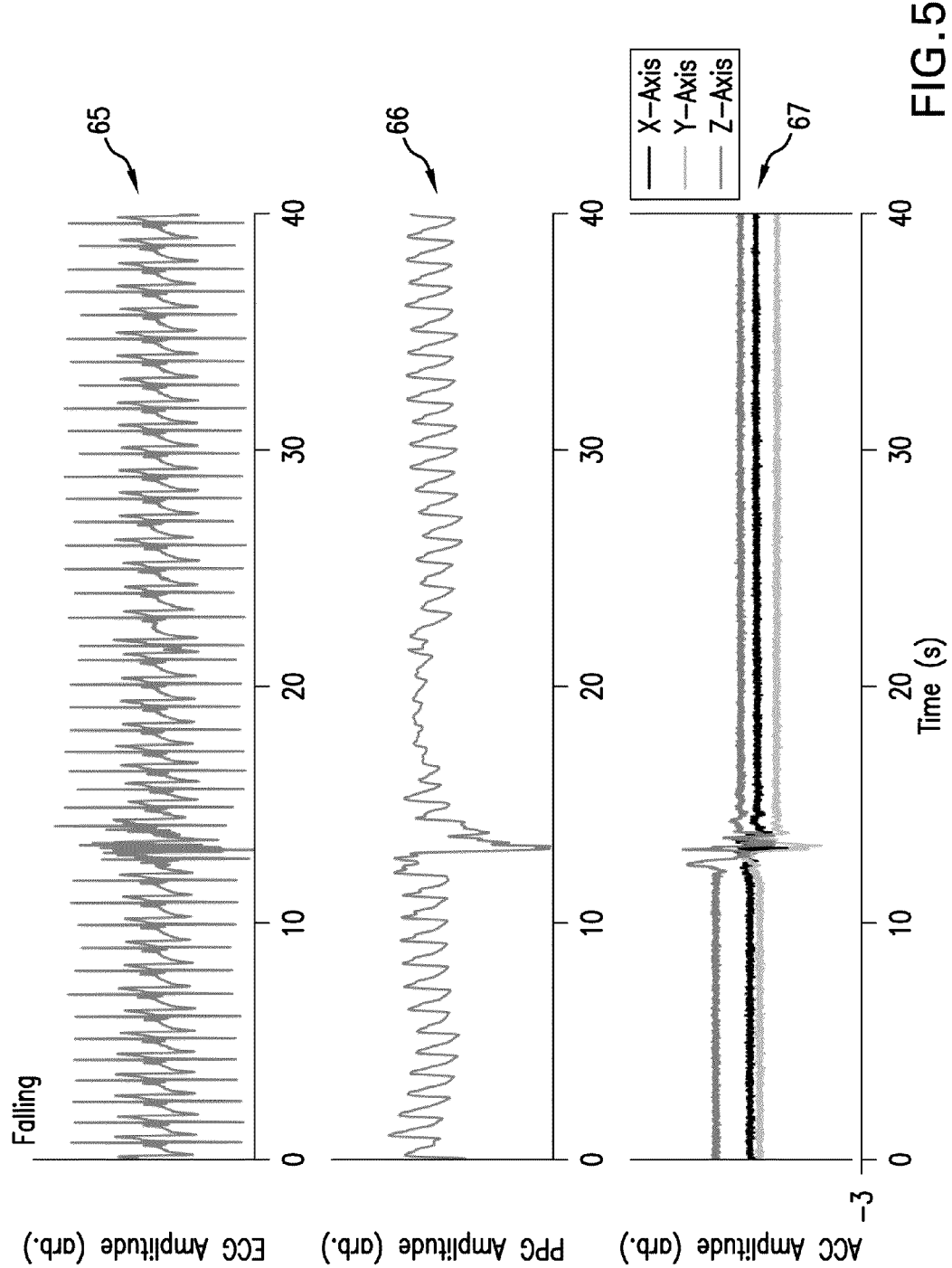
FIG. 5 shows a graph of time-dependent waveforms (ECG, PPG, and ACC) generated from a falling patient by, respectively, the ECG system, the optical system, and the accelerometer system of FIG. 1.
Figures 20A, 20B:
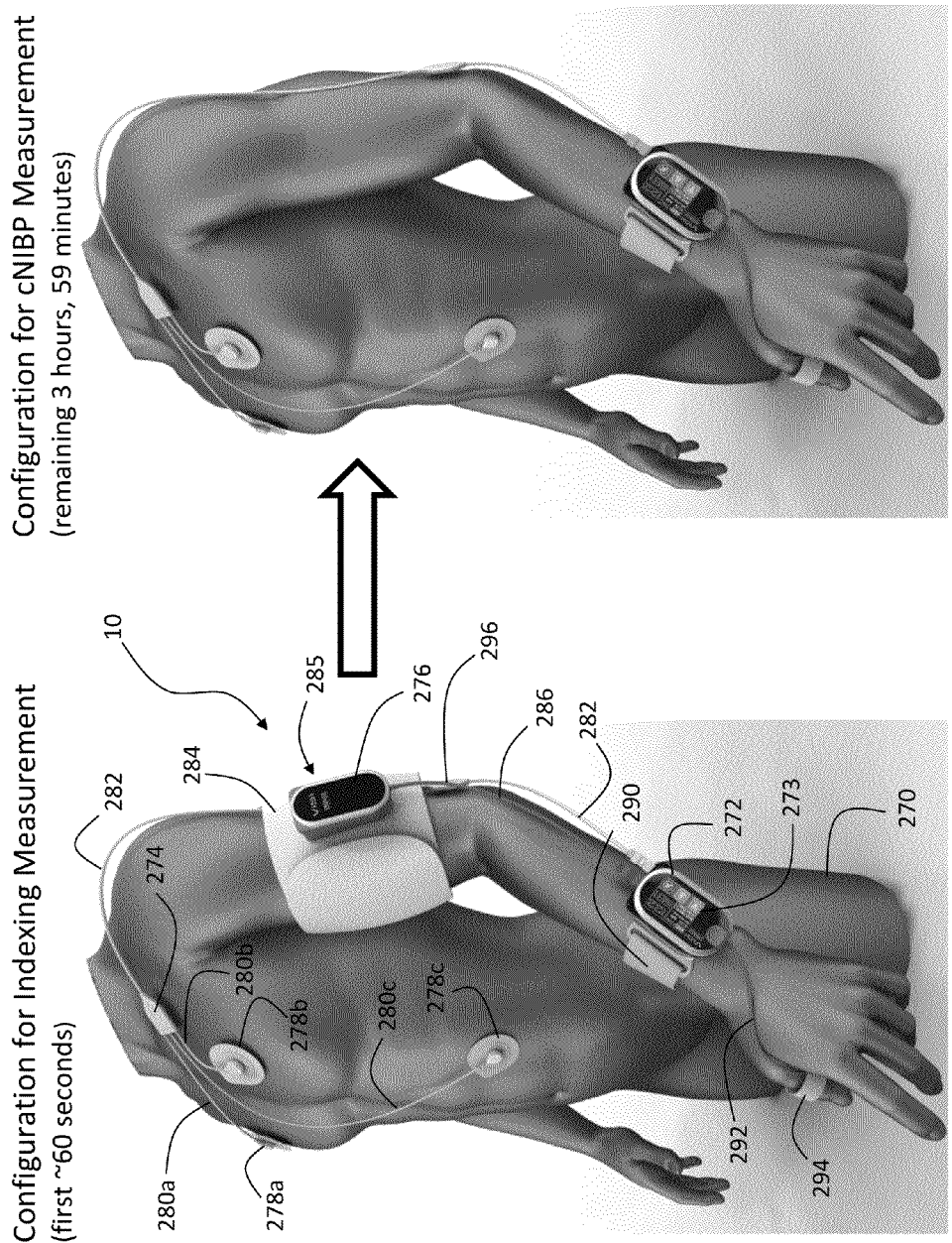
FIGS. 20A and 20B show images of the body-worn monitor of FIG. 1 attached to a patient with and without, respectively, a cuff-based pneumatic system used for a calibrating indexing measurement.
Figure 21:
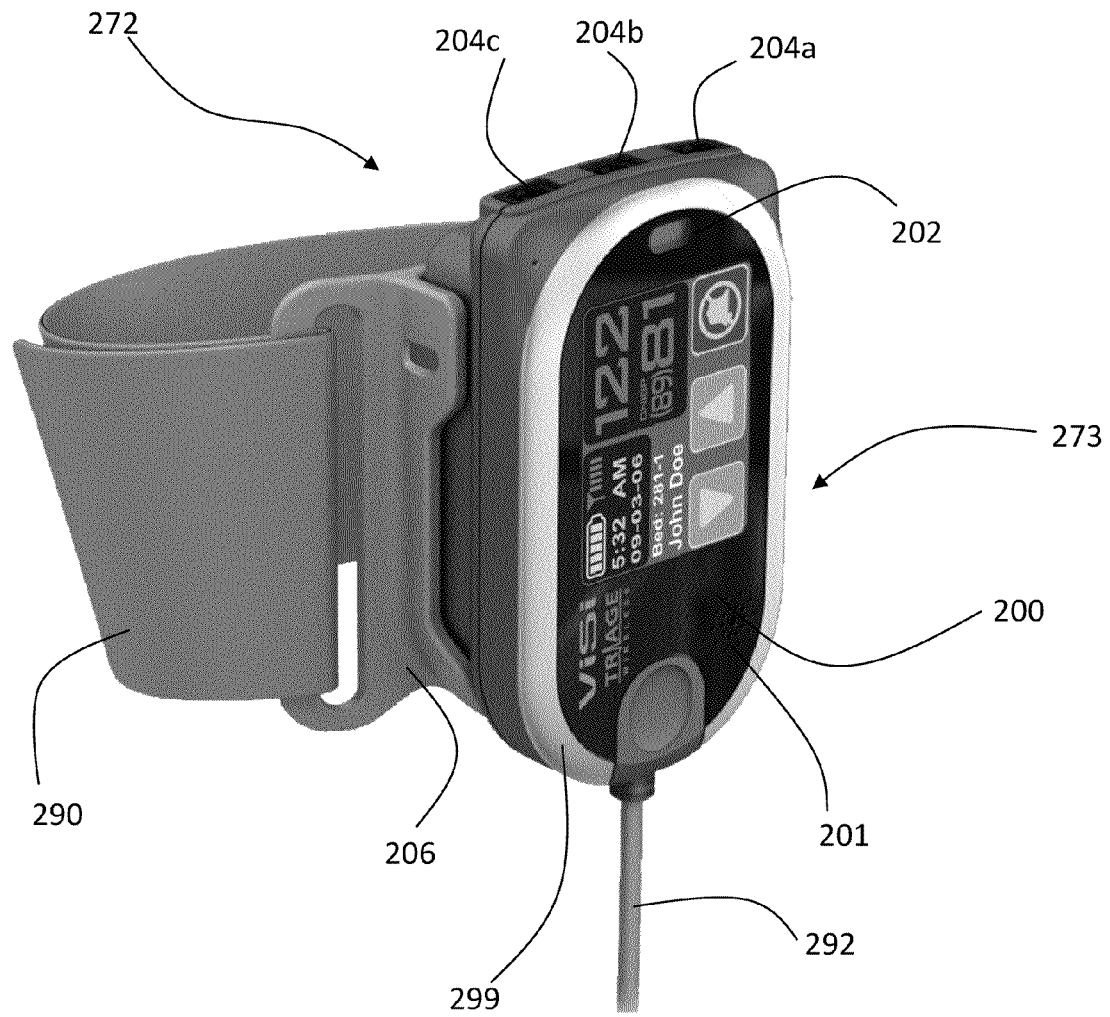
FIG. 21 shows an image of the wrist-worn transceiver featured in the body-worn monitor of FIGS. 20A and 20B.

FIGS. 2-5 show time-dependent graphs of ECG, PPG, and ACC waveforms for a patient who is resting (FIG. 2), walking (FIG. 3), convulsing (FIG. 4), and falling (FIG. 5). Each graph includes a single ECG waveform 50, 55, 60, 65, PPG waveform 51, 56, 61, 66, and three ACC waveforms 52, 57, 62, 67. The ACC waveforms correspond to signals measured along the x, y, and z axes by a single accelerometer worn on the patient's wrist (e.g., $ACC_{1-3}$). The body-worn monitor includes additional accelerometers (typically worn on the patient's bicep and chest) that measure the remaining six ACC waveforms (e.g., $ACC_{4-9}$). Sensors that measure the ECG, PPG, and ACC waveforms are shown in FIGS. 20A, 20B, and 21, and described in detail below.

The figures indicate that time-dependent properties of both ECG 50, 55, 60, 65 and PPG 51, 56, 61, 66 waveforms are strongly affected by motion, as indicated by the ACC waveforms 52, 57, 62, 67. Accuracy of the vital signs, such as SYS, DIA, heart rate, respiratory rate, and SpO2, calculated from these waveforms is therefore affected as well. Body temperature, which is measured from a separate body-worn sensor (typically a thermocouple) and does not rely on these waveforms, is relatively unaffected by motion.

Figure 2:
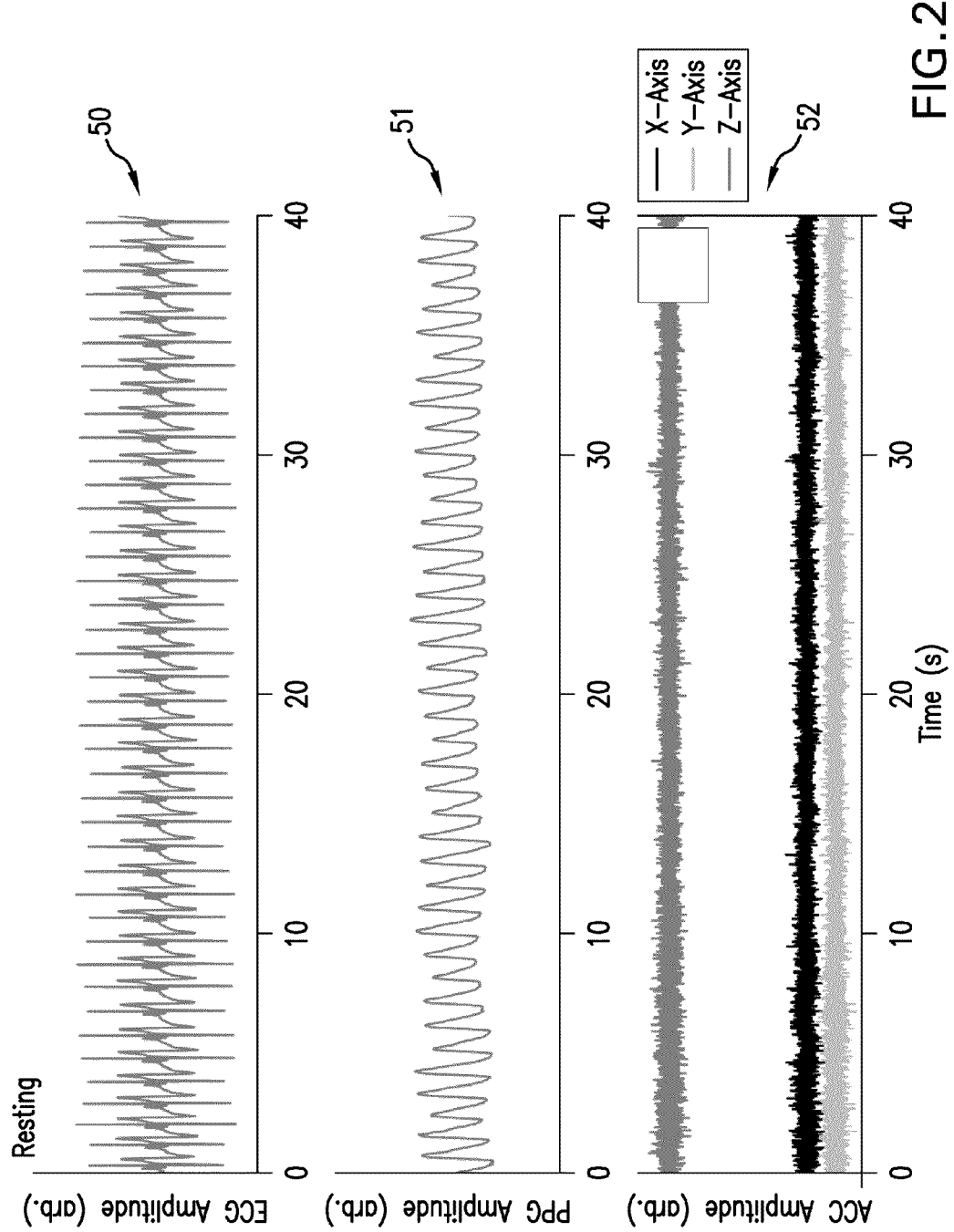
FIG. 2 shows a graph of time-dependent waveforms (ECG, PPG, and ACC) generated from a resting patient by, respectively, the ECG system, the optical system, and the accelerometer system of FIG. 1.

FIG. 2 shows data collected from a patient at rest. This state is clearly indicated by the ACC waveforms 52, which feature a relatively stable baseline. High-frequency noise in all the ACC waveforms 52, 57, 62, 67 shown in FIGS. 2-5 is due to electrical noise, and is not indicative of patient motion in any way. The ECG 50 and PPG 51 waveforms for this patient are correspondingly stable, thus allowing algorithms operating on the body-worn monitor to accurately determine heart rate and respiratory rate (from the ECG waveform 50), blood pressure (from a PTT extracted from both the ECG 50 and PPG 51 waveforms), and SpO2 (from PPG waveforms, similar to PPG waveform 51, measured at both 900 nm and 600 nm using the finger-worn optical sensor). Respiratory rate slightly modulates the envelope of the ECG 50 and PPG 51 waveforms. Based on the data shown in FIG. 2, algorithms operating on the body-worn monitor assume that vital signs calculated from a resting patient are relatively stable; the algorithm therefore deploys normal threshold criteria for alarms/alerts, described below in Table 2, for patients in this state.

FIG. 3 shows ECG 55, PPG 56, and ACC 57 waveforms measured from a walking patient wearing the body-worn monitor. In this case, the ACC waveform 57 clearly indicates a quasi-periodic modulation, with each 'bump' in the modulation corresponding to a particular step. The 'gaps' in the modulation, shown near 10, 19, 27, and 35 seconds, correspond to periods when the patient stops walking and changes direction. Each bump in the ACC waveform includes relatively high-frequency features (other than those associated with electrical noise, described above) that correspond to walking-related movements of the patient's wrist.

The ECG waveform 55 measured from the walking patient is relatively unaffected by motion, other than indicating an increase in heart rate (i.e., a shorter time separation between neighboring QRS complexes) and respiratory rate (i.e. a higher frequency modulation of the waveform's envelope) caused by the patient's exertion. The PPG waveform 56, in contrast, is strongly affected by this motion, and becomes basically immeasurable. Its distortion is likely due to a quasi-periodic change in light levels, caused by the patient's swinging arm, and detected by the optical sensor's photodetector. Movement of the patient's arm additionally affects blood flow in the thumb and can cause the optical sensor to move relative to the patient's skin. The photodetector measures all of these artifacts, along with a conventional PPG signal (like the one shown in FIG. 2) caused by volumetric expansion in the underlying arteries and capillaries within the patient's thumb. The artifacts produce radiation-induced photocurrent that is difficult to deconvolute from normal PPG signal used to calculate PTT-based blood pressure and SpO2. These vital signs, and particularly blood pressure because of its sensitivity to temporal separation from the ECG's QRS complex, are thus difficult to measure when the patient is walking.

The body-worn monitor deploys multiple strategies to avoid generating false alarms/alerts during a walking activity state. As described in detail below, the monitor can detect this state by processing the ACC waveforms shown in FIG. 3 along with similar waveforms measured from the patient's bicep and chest. As described in Table 1A, walking typically elevates heart rate, respiratory rate, and blood pressure, and thus alarm thresholds for these parameters are systematically and temporarily increased when this state is detected. Values above the modified thresholds are considered abnormal, and trigger an alarm. An accurate measurement of SpO2 depends on relative optical absorption measurements made at both 900 and 600 nm, and does not necessarily rely on having a PPG waveform that is completely free of motion-related artifacts. Still, it is more difficult to measure an accurate value of SpO2 when a patient is walking. Moreover, SpO2, unlike heart rate, respiratory rate and blood pressure, does not typically increase with exertion. Thus the alarm thresholds for this parameter, as shown in Table 1A, do not change when the patient is walking. Body temperature measured with the body-worn monitor typically increases between 1-5%, depending on the physical condition of the patient and the speed at which they are walking.

TABLE 1A motion-dependent alarm/alert thresholds and heuristic rules for a walking patient

| Vital Sign | Motion State | Modified Threshold for Alarms/Alerts | Heuristic Rules for Alarms/Alerts |
| --- | --- | --- | --- |
| Blood Pressure (SYS, DIA) | Walking | Increase (+10-30%) | Use Modified Threshold; Alarm/Alert if Value Exceeds Threshold |
| Heart Rate | Walking | Increase (+10-300%) | Ignore Threshold; Do Not Alarm/Alert |
| Respiratory Rate | Walking | Increase (+10-300%) | Ignore Threshold; Do Not Alarm/Alert |
| SpO2 | Walking | No Change | Ignore Threshold; Do Not Alarm/Alert |
| Temperature | Walking | Increase (+10-30%) | Use Original Threshold; Alarm/Alert if Value Exceeds Threshold |

To further reduce false alarms/alerts, software associated with the body-worn monitor or remote monitor can deploy a series of heuristic rules determined beforehand using practical, empirical studies. These rules, for example, can indicate that a walking patient is likely healthy, breathing, and characterized by a normal SpO2. Accordingly, the rules dictate that respiratory rate and SpO2 values that are measured during a walking state and exceed predetermined alarm/alert thresholds are likely corrupted by artifacts; the system, in turn, does not sound the alarm/alert in this case. Heart rate, as indicated by FIG. 2, and body temperature can typically be accurately measured even when a patient is walking; the heuristic rules therefore dictate that alarms/alerts can be generated from these vital signs, but that the modified thresholds listed in Table 1A be used for this process.

FIG. 4 shows ECG 60, PPG 61, and ACC 62 waveforms measured from a patient that is simulating convulsing by rapidly moving their arm back and forth. A patient undergoing a Grand-mal seizure, for example, would exhibit this type of motion. As is clear from the waveforms, the patient is at rest for the initial 10 seconds shown in the graph, during which the ECG 60 and PPG 61 waveforms are uncorrupted by motion. The patient then begins a period of simulated, rapid convulsing that lasts for about 12 seconds. A brief 5-second period of rest follows, and then convulsing begins for another 12 seconds or so.

Convulsing modulates the ACC waveform 62 due to rapid motion of the patient's arm, as measured by the wrist-worn accelerometer. This modulation is strongly coupled into the PPG waveform 61, likely because of the phenomena described above, i.e.: 1) ambient light coupling into the optical sensor's photodiode; 2) movement of the photodiode relative to the patient's skin; and 3) disrupted blow flow underneath the optical sensor. Note that from about 23-28 seconds the ACC waveform 62 is not modulated, indicating that the patient's arm is at rest. During this period the ambient light is constant and the optical sensor is stationary relative to the patient's skin. But the PPG waveform 61 is still strongly modulated, albeit at a different frequency than the modulation that occurred when the patient's arm was moving. This indicates modulation of the PPG waveform 61 is likely caused by at least the three factors described above, and that disrupted blood flow underneath the optical sensor continues even after the patient's arm stops moving. Using this information, both ECG and PPG waveforms similar to those shown in FIG. 4 can be analyzed in conjunction with ACC waveforms measured from groups of stationary and moving patients. These data can then be analyzed to estimate the effects of specific motions and activities on the ECG and PPG waveforms, and then deconvolute them using known mathematical techniques to effectively remove any motion-related artifacts. The deconvoluted ECG and PPG waveforms can then be used to calculate vital signs, as described in detail below.

The ECG waveform 60 is modulated by the patient's arm movement, but to a lesser degree than the PPG waveform 61. In this case, modulation is caused primarily by electrical 'muscle noise' instigated by the convulsion and detected by the ECG electrodes, and well as by convulsion-induced motion in the ECG cables and electrodes relative to the patient's skin. Such motion is expected to have a similar affect on temperature measurements, which are determined by a sensor that also includes a cable.

Table 1B, below, shows the modified threshold values and heuristic rules for alarms/alerts generated by a convulsing patient. In general, when a patient experiences convulsions, such as those simulated during the two 12-second periods in FIG. 4, it is virtually impossible to accurately measure any vital signs from the ECG 60 and PPG 61 waveforms. For this reason the threshold values corresponding to each vital sign are not adjusted when convulsions are detected. Heart rate determined from the ECG waveform, for example, is typically erroneously high due to high-frequency convulsions, and respiratory rate is immeasurable from the distorted waveform. Strong distortion of the optical waveform also makes both PPT-based blood pressure and SpO2 difficult to measure. For this reason, algorithms operating on either the body-worn monitor or a remote monitor will not generate alarms/alerts based on vital signs when a patient is convulsing, as these vital signs will almost certainly be corrupted by motion-related artifacts.

TABLE 1B motion-dependent alarm/alert thresholds and heuristic rules for a convulsing patient

| Vital Sign | Motion State | Modified Threshold for Alarms/Alerts | Heuristic Rules for Alarms/Alerts |
| --- | --- | --- | --- |
| Blood Pressure (SYS, DIA) | Convulsing | No Change | Ignore Threshold; Generate Alarm/Alert Because of Convulsion |

TABLE 1B-continued motion-dependent alarm/alert thresholds and
heuristic rules for a convulsing patient

| Vital Sign | Motion State | Modified Threshold for Alarms/Alerts | Heuristic Rules for Alarms/Alerts |
|---|---|---|---|
| Heart Rate | Convulsing | No Change | Ignore Threshold; Generate Alarm/Alert Because of Convulsion |
| Respiratory Rate | Convulsing | No Change | Ignore Threshold; Generate Alarm/Alert Because of Convulsion |
| SpO2 | Convulsing | No Change | Ignore Threshold; Generate Alarm/Alert Because of Convulsion |
| Temperature | Convulsing | No Change | Ignore Threshold; Generate Alarm/Alert Because of Convulsion |

Table 1B also shows the heuristic rules for convulsing patients. Here, the overriding rule is that a convulsing patient needs assistance, and thus an alarm/alert for this patient is generated regardless of their vital signs (which, as described above, are likely inaccurate due to motion-related artifacts). The system always generates an alarm/alert for a convulsing patient.

FIG. 5 shows ECG 65, PPG 66, and ACC 67 waveforms measured from a patient that experiences a fall roughly 13 seconds into the measuring period. The ACC waveform 67 clearly indicates the fall with a sharp decrease in its signal, followed by a short-term oscillatory signal, due (literally) to the patient bouncing on the floor. After the fall, ACC waveforms 67 associated with the x, y, and z axes also show a prolonged decrease in value due to the resulting change in the patient's posture. In this case, both the ECG 65 and PPG 66 waveforms are uncorrupted by motion prior to the fall, but basically immeasurable during the fall, which typically takes only 1-2 seconds. Specifically, this activity adds very high frequency noise to the ECG waveform 65, making it impossible to extract heart rate and respiratory rate during this short time period. Falling causes a sharp drop in the PPG waveform 66, presumably for the same reasons as described above (i.e. changes in ambient light, sensor movement, disruption of blood flow) for walking and convulsing.

After a fall, both the ECG 65 and PPG 66 waveforms are free from artifacts, but both indicate an accelerated heart rate and relatively high heart rate variability for roughly 10 seconds. During this period the PPG waveform 66 also shows a decrease in pulse amplitude. Without being bound to any theory, the increase in heart rate may be due to the patient's baroreflex, which is the body's hemostatic mechanism for regulating and maintaining blood pressure. The baroreflex, for example, is initiated when a patient begins faint. In this case, the patient's fall may cause a rapid drop in blood pressure, thereby depressing the baroreflex. The body responds by accelerating heart rate (indicated by the ECG waveform 65) and increasing blood pressure (indicated by a reduction in PTT, as measured from the ECG 65 and PPG 66 waveforms) in order to deliver more blood to the patient's extremities.

Table 1C shows the heuristic rules and modified alarm thresholds for a falling patient. Falling, similar to convulsing, makes it difficult to measure waveforms and the vital signs calculated from them. Because of this and the short time duration associated with a fall, alarms/alerts based on vital signs thresholds are not generated when a patient falls. However, this activity, optionally coupled with prolonged stationary period or convulsion (both determined from the following ACC waveform), generates an alarm/alert according to the heuristic rules.

TABLE 1C motion-dependent alarm/alert thresholds
and heuristic rules for a falling patient

| Vital Sign | Motion State | Modified Threshold for Alarms/Alerts | Heuristic Rules for Alarms/Alerts |
|---|---|---|---|
| Blood Pressure (SYS, DIA) | Falling | No Change | Ignore Threshold; Generate Alarm/Alert Because of Fall |
| Heart Rate | Falling | No Change | Ignore Threshold; Generate Alarm/Alert Because of Fall |
| Respiratory Rate | Falling | No Change | Ignore Threshold; Generate Alarm/Alert Because of Fall |
| SpO2 | Falling | No Change | Ignore Threshold; Generate Alarm/Alert Because of Fall |
| Temperature | Falling | No Change | Ignore Threshold; Generate Alarm/Alert Because of Fall |

Figure 6:
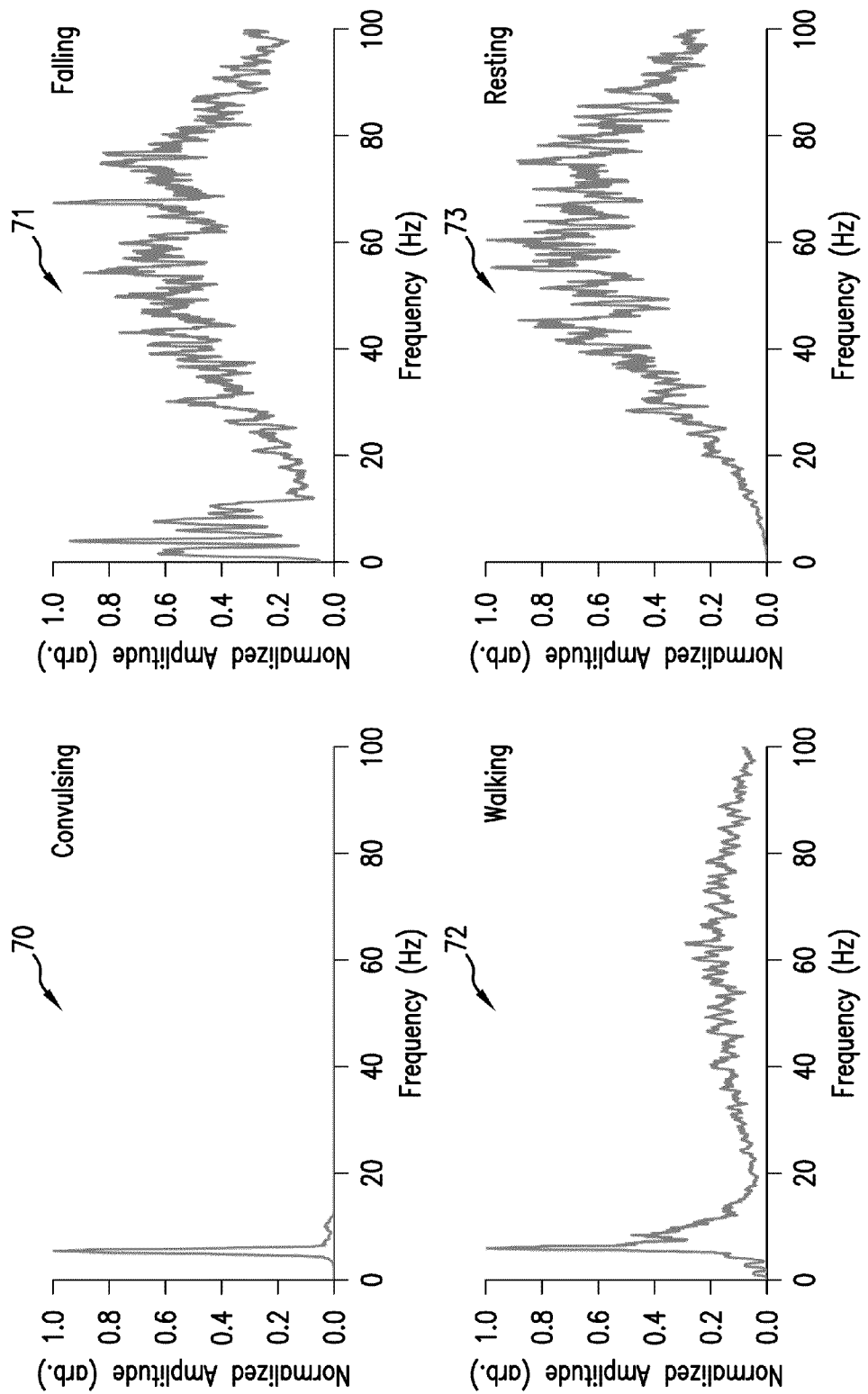
FIG. 6 shows graphs of frequency-dependent power spectra generated from the time-dependent ACC waveforms of FIGS. 2-5.

As described in detail below, the patient's specific activity relates to both the time-dependent ACC waveforms and the frequency-dependent Fourier Transforms of these waveforms. FIG. 6, for example, shows power spectra 70, 71, 72, 73 corresponding to ACC waveforms generated during, respectively, convulsing, falling, walking, and resting. These power spectra were generated from both real and imaginary components of Fourier Transforms calculated from the corresponding time-dependent waveforms.

The ACC waveform corresponding to a resting patient (52 in FIG. 2) lacks any time-dependent features corresponding to patient motion; the high-frequency features in this waveform (i.e., those greater than about 20 Hz) are due solely to electrical noise generated by the accelerometer. The power spectrum 73 shown in the lower right-hand corner of FIG. 6 thus lacks any features in a frequency range (typically less than 20 Hz) corresponding to human motion. In contrast, convulsing typically represents a well-defined, quasi-periodic motion; this corresponds to a strong, narrow peak occurring near 6 Hz that dominates the power spectrum 70 shown in the upper left-hand corner of the figure. The bandwidth of this peak, which is best represented by a Gaussian function, indicates a distribution of frequencies centered around 6 Hz. Falling and walking, as indicated by spectra 71, 72 shown, respectively, in the upper right-hand and lower left-hand portions of the figure, are more complicated motions. The spectrum for walking, for example, is characterized by relatively weak peaks occurring near 1 and 2 Hz; these correspond to frequencies associated with the patient's stride. A relatively large peak in the spectrum near 7 Hz corresponds to higher frequency motion of the patient's hand and arm that naturally occurs during walking. Falling, unlike walking or convulsing, lacks any well-defined periodic motion. Instead it is characterized by a sharp time-dependent change in the ACC waveform (67 in FIG. 5). This event is typically composed of a collection of relatively high-frequency components, as indicated by the multiple harmonic peaks, ranging every 2 Hz, between 2-12 Hz. Note that the spectral power associated with convulsions 70 is significantly higher than that associated with both falling 71 and walking 72. For this reason the higher frequency spectral components associated with the accelerometer's electrical noise, shown clearly in the resting power spectrum 73, are evident in these spectra 71, 72, but not in the spectrum 70 for convulsions.

Figure 7:
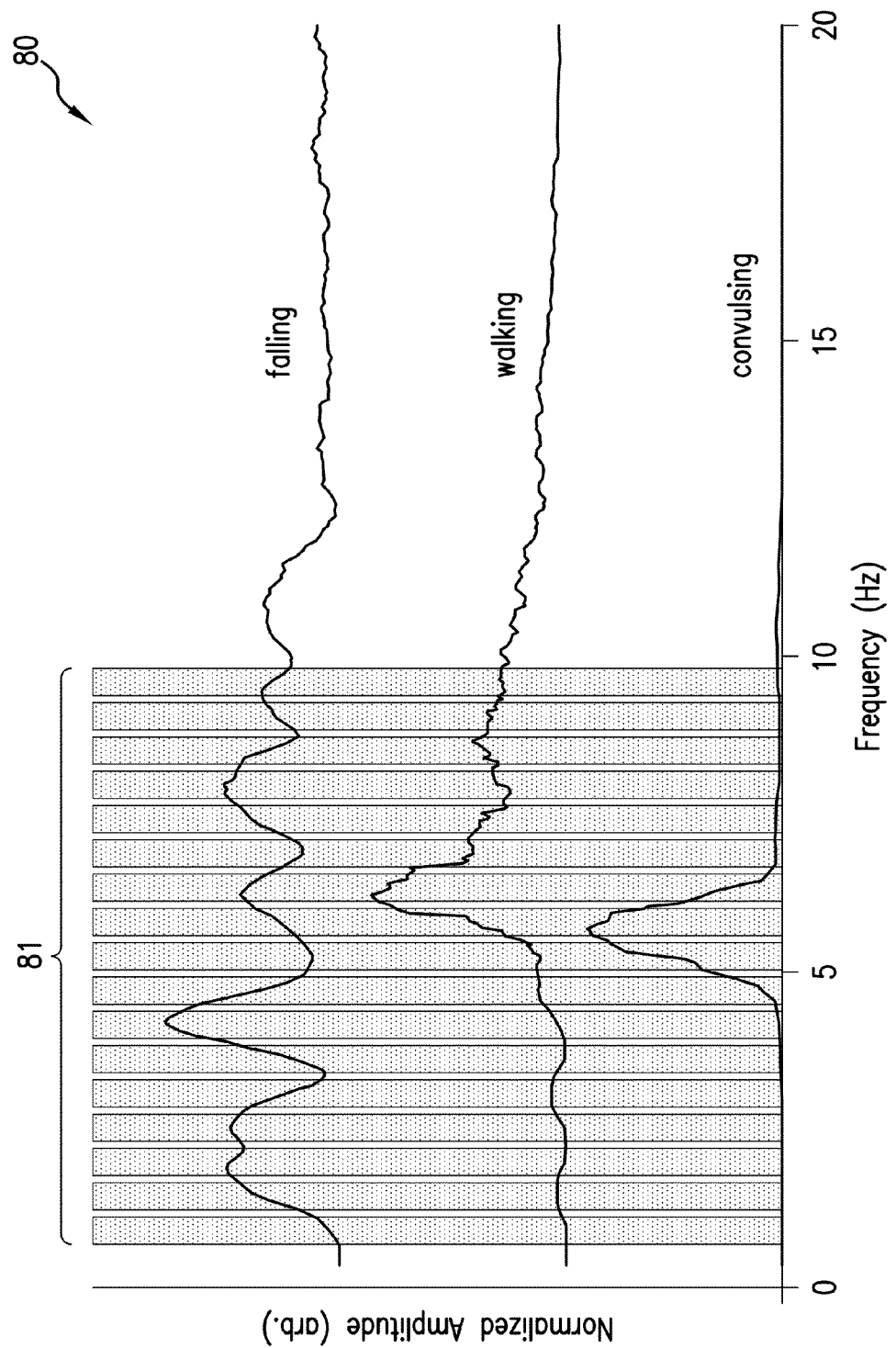
FIG. 7 shows a graph of the first 20 Hz of three of the frequency-dependent power spectra of FIG. 6.

FIG. 7 shows a graph 80 of frequency-dependent power spectra between 0-20 Hz of the falling, walking, and convulsing activities indicated in FIG. 6. This frequency range, as described above, corresponds to human motion. The graph 80 additionally includes a series of bars 81 divided into roughly 0.5 Hz increments that extend up to 10 Hz. The power of the individual spectra in these increments, as indicated by Table 5 and used in equations (36) and (37) below, can be processed along with time-dependent features of the ACC waveforms to estimate the patient's specific activity level. The distribution of frequencies in the graph 80 indicates, to some extent, how this algorithm works. For example, convulsing is typically characterized by a single well-defined frequency, in this case centered near 6 Hz. This activity has a bandwidth of approximately 1.5 Hz, and therefore yields a relatively high power for the spectral increments in this range. Falling, in contrast, yields relatively equivalent power in increments ranging from 2 to 10 Hz. The power spectrum corresponding to walking is relatively complex, resulting measurable power in low-frequency increments (typically 1-2 Hz, due to the patient's stride), and higher power in relatively high-frequency increments (near 7 Hz, due to the patient's hand and arm motion). To characterize a patient's activity, a model is built by analyzing activities from a collection of patients from a variety of demographics, and then analyzing these data with a statistical approach, as described in detail below.

Life-Threatening Alarms/Alerts

ASY and VFIB are typically determined directly from the ECG waveform using algorithms known in the art. To reduce false alarms associated with these events, the body-worn monitor calculates ASY and VFIB from the ECG waveform, and simultaneously determines a 'significant pulse' from both the PPG waveform and cNIBP measurement, described below. A significant pulse occurs when the monitor detects a pulse rate from the PPG waveform (see, for example, 51 in FIG. 2) ranging from 30-150 bpm, and a pulse pressure separating SYS and DIA greater than 30 mmHg. When ASY and VFIB are detected from the ECG waveform, the monitor continuously checks for a significant pulse and compares the patient's current pulse rate to that measured during the entire previous 60 seconds. The alarm/alert related to ASY and VFIB are delayed, typically by 10-20 seconds, if the pulse is significant and the pulse rate measured during this period differs from patient's current pulse rate by less than 40%. The monitor sounds an alarm/alert if ASY and VFIB measured from the ECG waveform persists after the delay period. The alarm/alert is not generated if ASY and VFIB are no longer detected after the delay period.

The alarm/alert for ASY and VFIB additionally depends on the patient's activity level. For example, if the monitor determines ASY and VFIB from the ECG, and that the patient is walking from the ACC waveforms, it then checks for a significant pulse and determines pulse rate from the PPG waveform. In this situation the patient is assumed to be in an activity state prone to false alarms. The alarms/alerts related to ASY and VFIB are thus delayed, typically by 20-30 seconds, if the monitor determines the patient's pulse to be significant and their current pulse differs from their pulse rate measured during the previous 60 seconds by less than 40%. The monitor sounds an alarm only if ASY and VFIB remain after the delay period and once the patient stops walking. In another embodiment, an alarm/alert is immediately sounded if the monitor detects either ASY or VFIB, and no significant pulse is detected from the PPG waveform for between 5-10 seconds.

The methodology for alarms/alerts is slightly different for VTAC due to the severity of this condition. VTAC, like ASY and VFIB, is detected directly from the ECG waveform using algorithms know in the art. This condition is typically defined as five or more consecutive premature ventricular contractions (PVCs) detected from the patient's ECG. When VTAC is detected from the ECG waveform, the monitor checks for a significant pulse and compares the patient's current pulse rate to that measured during the entire previous 60 seconds. The alarm/alert related to VTAC is delayed, typically by 20-30 seconds, if the pulse is determined to be significant and the pulse rate measured during this period differs from patient's current pulse rate by less than 25%. The monitor immediately sounds an alarm/alert if VTAC measured from the ECG waveform meets the following criteria: 1) its persists after the delay period; 2) the deficit in the pulse rate increases to more than 25% at any point during the delay period; and 3) no significant pulse is measured for more than 8 consecutive seconds during the delay period. The alarm for VTAC is not generated if any of these criteria are not met.

APNEA refers to a temporary suspension in a patient's breathing and is determined directly from respiratory rate. The monitor measures this vital sign from the ECG waveform using techniques called 'impedance pneumography' or 'impedance rheography', both of which are known in the art. The monitor sounds an alarm/alert only if APNEA is detected and remains (i.e. the patient does not resume normal breathing) for a delay period of between 20-30 seconds.

The monitor does not sound an alarm/alert if it detects ASY, VFIB, VTAC, or APNEA from the ECG waveform and the patient is walking (or experiencing a similar motion that, unlike falling or convulsing, does not result in an immediate alarm/alert). The monitor immediately sounds an alarm during both the presence and absence of these conditions if it detects that the patient is falling, has fell and remains on the ground for more than 10 seconds, or is having a Grand-mal seizure or similar convulsion. These alarm criteria are similar to those described in the heuristic rules, above.

Threshold Alarms/Alerts

Threshold alarms are generated by comparing vital signs measured by the body-worn monitor to fixed values that are either preprogrammed or calculated in real time. These threshold values are separated, as described below, into both outer limits (OL) and inner limits (IL). The values for OL are separated into an upper outer limit (UOL) and a lower outer limit (LOL). Default values for both UOL and LOL are typically preprogrammed into the body-worn monitor during manufacturing, and can be adjusted by a medical professional once the monitor is deployed. Table 2, below, lists typical default values corresponding to each vital sign for both UOL and LOL.

Values for IL are typically determined directly from the patient's vital signs. These values are separated into an upper inner limit (UIL) and a lower inner limit (LIL), and are calculated from the UOL and LOL, an upper inner value (UIV), and a lower inner value (LIV). The UIV and LIV can either be preprogrammed parameters (similar to the UOL and LOL, described above), or can be calculated directly from the patient's vital signs using a simple statistical process described below:

$$UIL = UIV + (UOL - UIV)/3$$

(option A): UIV→preset factory parameter adjusted by medical professional
(option B): UIV→1.3×weighted average of vital sign over previous 120 s $$LIL = LIV + (LOL - LIV)/3$$

(option A): LIV→preset factory parameter adjusted by medical professional
(option B): LIV→0.7×weighted average of vital sign over previous 120 s In a preferred embodiment the monitor only sounds an alarm/alert when the vital sign of issue surpasses the UOL/

LOL and the UIL/LIL for a predetermined time period. Typically, the time periods for the UOL/LOL are shorter than those for the UIL/LIL, as alarm limits corresponding to these extremities represent a relatively large deviation for normal values of the patient's vital signs, and are therefore considered to be more severe. Typically the delay time periods for alarms/alerts associated with all vital signs (other than temperature, which tends to be significantly less labile) are 10 s for the UOL/LOL, and 120-180 s for the UIL/LIL. For temperature, the delay time period for the UOL/LOL is typically 600 s, and the delay time period for the UIL/LIL is typically 300 s.

Other embodiments are also possible for the threshold alarms/alerts. For example, the body-worn monitor can sound alarms having different tones and durations depending if the vital sign exceeds the UOL/LOL or UIL/LIL. Similarly, the tone can be escalated (in terms of acoustic frequency, alarm 'beeps' per second, and/or volume) depending on how long, and by how much, these thresholds are exceeded. Alarms may also sound due to failure of hardware within the body-worn monitor, or if the monitor detects that one of the sensors (e.g. optical sensor, ECG electrodes) becomes detached from the patient.

both the time-dependent ACC waveforms and their power spectra. For example, the power spectra of ACC waveforms corresponding to a patient lying on their back will have essentially the same AC values compared to those measured when the patient is lying on their side. However, due to the relative positioning of their limbs in these two states, the DC values of the time-dependent ACC waveforms will differ. This means these two states can likely be distinguished. In contrast, a patient brushing their teeth will exhibit both time-dependent ACC waveforms and associated power spectra that are virtually identical to those of a patient having a Grand-mal seizure. For this reason these two activity states cannot likely be distinguished.

The first module 94 corresponds to a resting patient. In this state, the patient generates ECG, PPG, and ACC waveforms similar to those shown in FIG. 2. The module 94 processes motion and vital sign information extracted from these waveforms to determine if the patient is indeed resting. If so, the module 94 uses the threshold alarm/alert criteria for each vital sign described in Table 2. If the module 94 determines that the patient is not resting, the algorithm 85 progresses to the next module 95, which analyzes the motion data to determine if the patient is walking. If so, the module 95 uses the heuristic

TABLE 2 default alarm/alert values for UOL, UIV, LIV,
and LOL Algorithm for Generating Alarms/Alerts

| Vital Sign | Default Upper Outer Limit (UOL) | Default Upper Inner Value (UIV) | Default Lower Inner Value (LIV) | Default Lower Outer Limit (LOL) |
|---|---|---|---|---|
| Blood Pressure (SYS) | 180 mmHg | 160 mmHg | 90 mmHg | 80 mmHg |
| Blood Pressure (MAP) | 130 mmHg | 120 mmHg | 70 mmHg | 60 mmHg |
| Blood Pressure (DIA) | 120 mmHg | 110 mmHg | 60 mmHg | 50 mmHg |
| Heart Rate | 150 bpm | 135 bpm | 45 bpm | 40 bpm |
| Respiratory Rate | 30 bmp | 25 bmp | 7 bpm | 5 bpm |
| SpO2 | 100% O2 | 90% O2 | 93% O2 | 85% O2 |
| Temperature | 103 deg. F. | 101 deg. F. | 95 deg. F. | 96.5 deg. F. |

Figure 8:
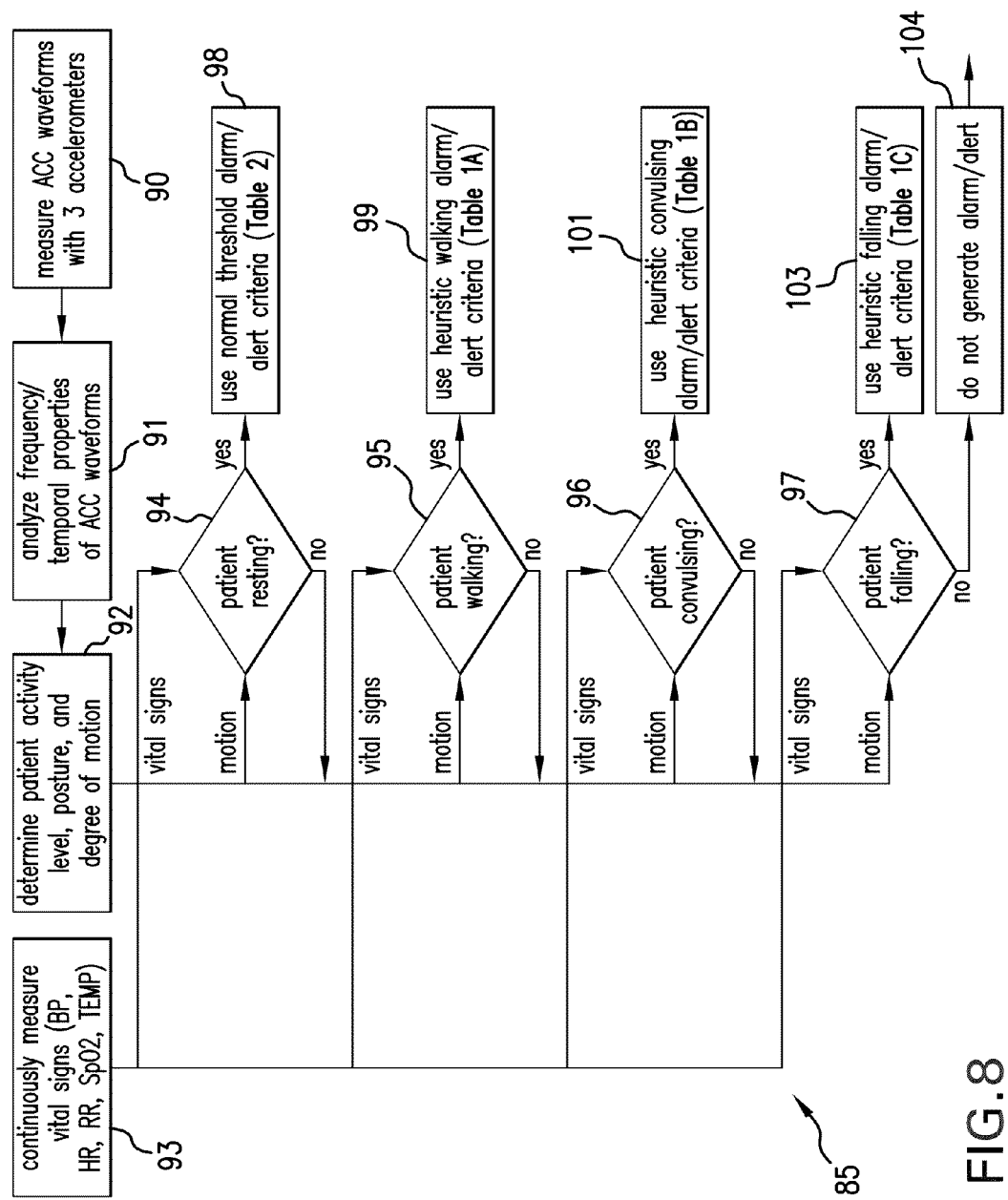
FIG. 8 shows a flow chart describing an algorithm used to generate alarms/alerts using the body-worn monitor of FIG. 1.

FIG. 8 shows a flow chart describing a high-level algorithm 85 for processing a patient's vital signs, along with their motion and activity level, to generate alarms/alerts for a hospitalized patient. It begins with continuously measuring the patient's vital signs with the body-worn monitor, optical sensor, and ECG electrodes, which are worn, respectively, on the patient's wrist, thumb, and chest (step 93). Simultaneously, three accelerometers associated with the monitor measure time-dependent ACC waveforms from the patient's wrist, bicep, and chest (step 90). The algorithm 85 determines the frequency-dependent power spectra of the ACC waveforms, and then analyzes the waveforms' temporal and frequency content (step 91). A statistical model, described in detail below, processes this information to determine patient's activity level, posture, and degree of motion (step 92). Once this information is determined, the algorithm processes it to generate a high percentage of 'true positive' alarms/alerts for one or more hospitalized patients. This is done with a series of separate algorithmic modules 94, 95, 96, 97 within the algorithm 85, with each module corresponding to a different activity state. Note that the algorithm 85 shown in FIG. 8 includes four modules (corresponding to resting, walking, convulsing, and falling), but more could be added, presuming they could accurately identify a specific activity state. Ultimately this depends how well a ROC curve (similar to those shown below in FIGS. 19A, B) associated with the specific activity state can predict the activity. The nature of these curves, in turn, depends on the uniqueness of activity-dependent features in alarm/alert criteria described in Table 1A, and if necessary generates an alarm/alert based on the patient's vital signs (step 99). If the module 95 determines that the patient is not walking, the algorithm 85 progresses to the next module 96, which determines if the patient is convulsing (e.g. having a Grand-mal seizure). If so, the module 95 uses the heuristic alarm/alert criterion described in Table 1B (step 101). This criterion ignores any alarm/alert threshold values, and automatically generates an alarm/alert because of the convulsing patient. Finally, if the module 95 determines that the patient is not convulsing, the algorithm 85 proceeds to the next module 97, which determines if the patient is falling. If the patient has fallen the algorithm uses the heuristic alarm/alert criterion described in Table 1C, which, like step 101, ignores any threshold values and automatically generates an alarm/alert (step 103). If the module 97 determines that the patient has not fallen, the algorithm 85 does not generate any alarm/alert, and the process is repeated, beginning with steps 90 and 93. In a typical embodiment, the algorithm 85 is repeated every 10-20 seconds using computer code operating on the body-worn monitor.

Method for Displaying Alarms/Alerts Using Graphical User Interfaces

Figure 9:
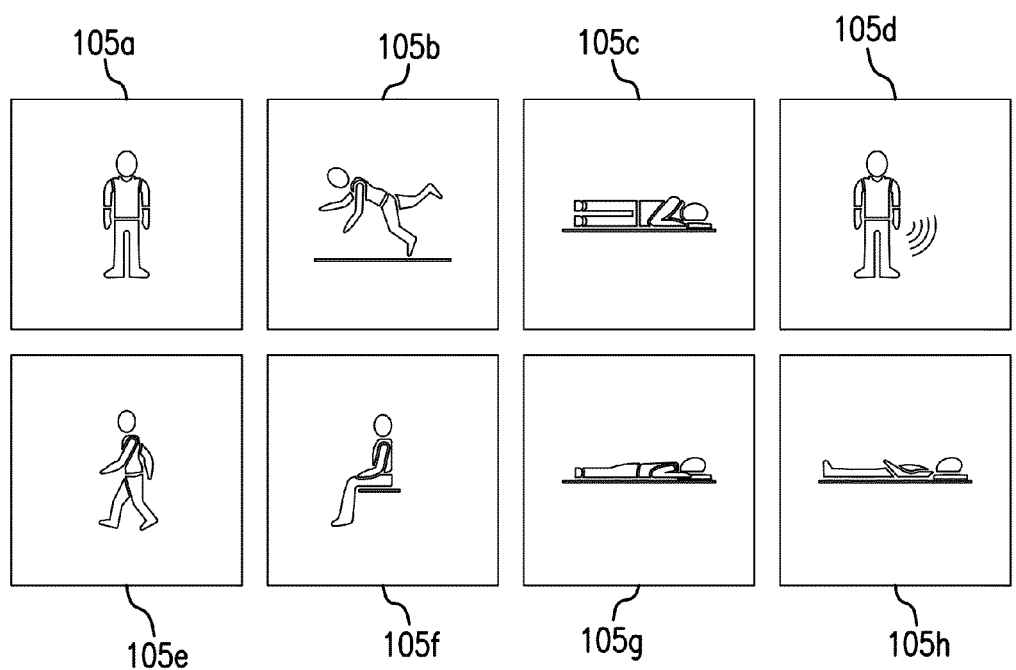
FIG. 9 shows a series of icons used to indicate different types of patient motion in graphical user interfaces (GUI) rendered on the body-worn monitor and remote monitor.
Figure 10A:
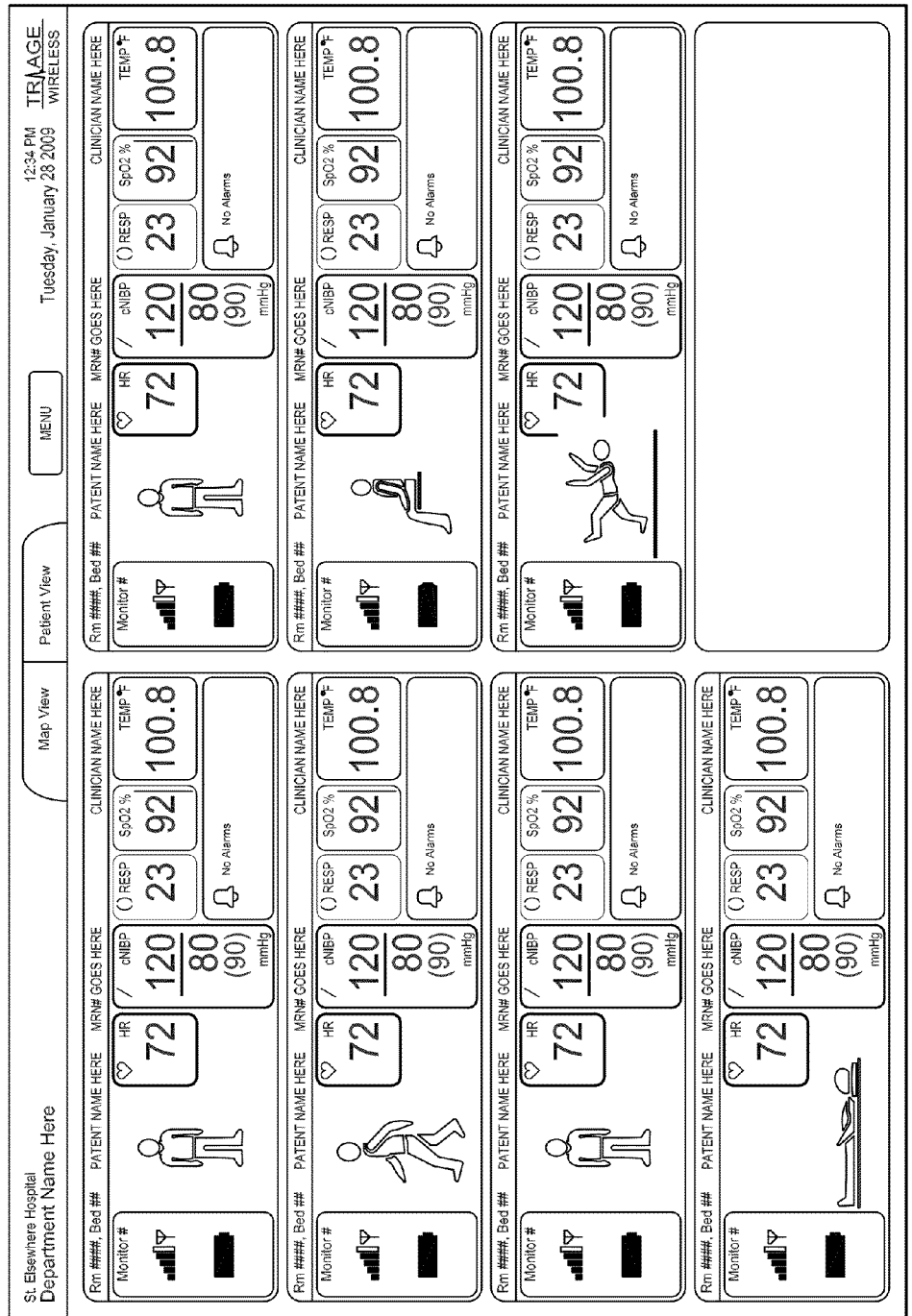
FIGS. 10A and 10B show, respectively, patient and map views used in the GUI rendered on the remote monitor.

Graphical user interfaces (GUI) operating on both the body-worn module and the remote monitor can render graphical icons that clearly identify the above-described patient activity states. FIG. 9 shows examples of such icons 105a-h, and Table 3, below, describes how they correspond to specific patient activity states. As shown in FIGS. 10A, B and 11A, B, these icons are used in GUIs for both the body-worn monitor and remote monitor.

TABLE 3 description of icons shown in FIG. 9 and used in GUIs for both body-worn monitor and remote monitor

| Icon | Activity State |
| --- | --- |
| 105a | Standing |
| 105b | Falling |
| 105c | resting; lying on side |
| 105d | Convulsing |
| 105e | Walking |
| 105f | Sitting |
| 105g | resting; lying on stomach |
| 105h | resting; lying on back |

Figure 10B:
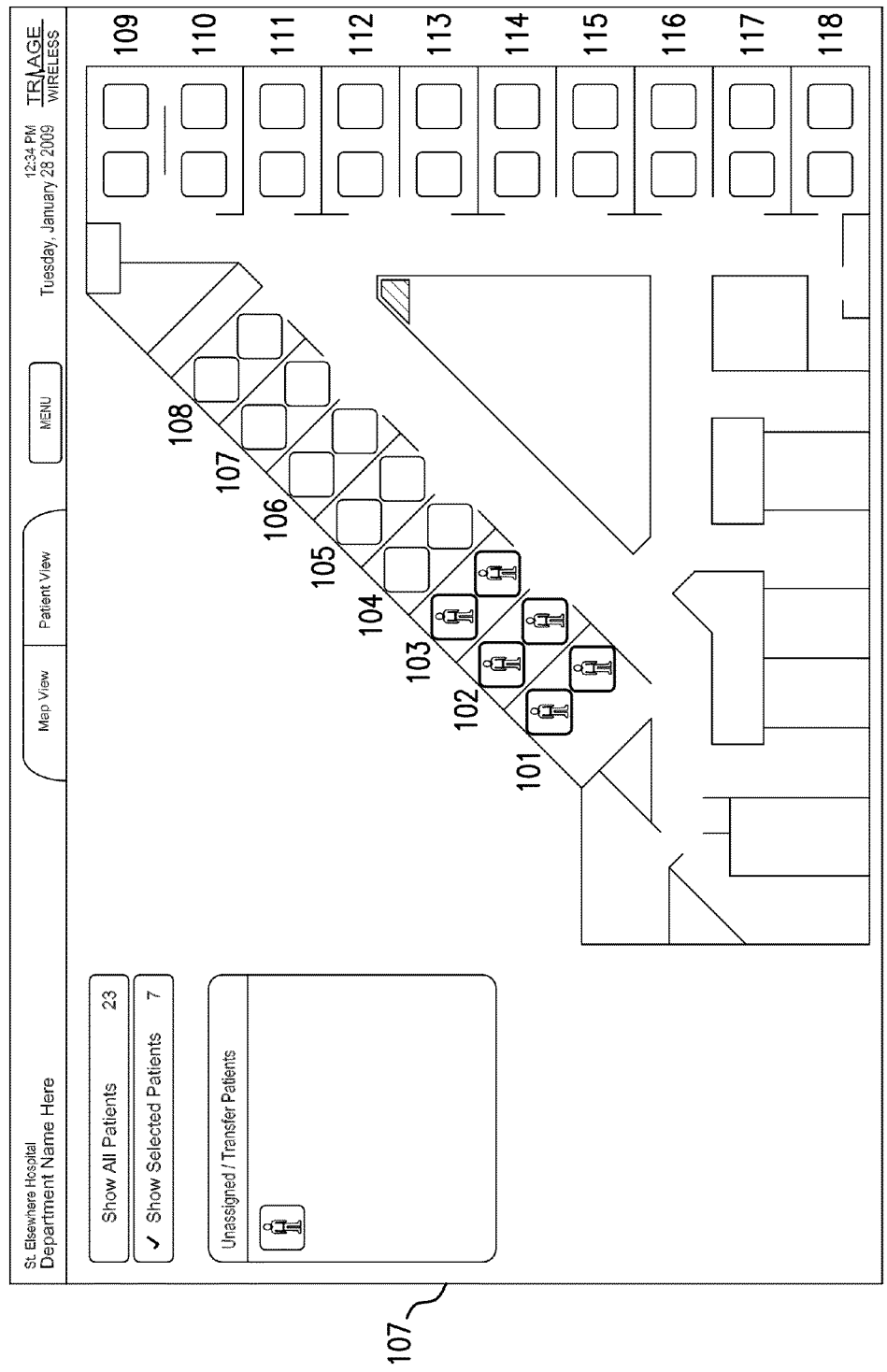

FIGS. 10A and 10B show patient (106 in FIG. 10A) and map (107 in FIG. 10B) views from a GUI typically rendered on a remote monitor, such as a monitoring station deployed at a central nursing station in the hospital. The remote monitor simultaneously communicates with multiple body-worn monitors, each deployed on a patient in an area of the hospital (e.g. a bay of hospital beds, or an ED). The body-worn monitors communicate through an interface that typically includes both wireless and wired components.

The patient view 106 is designed to give a medical professional, such as a nurse or doctor, a quick, easy-to-understand status of all the patients of all the patients in the specific hospital area. In a single glance the medical professional can determine their patients' vital signs, measured continuously by the body-worn monitor, along with their activity state and alarm status. The view 106 features a separate area 108 corresponding to each patient. Each area 108 includes text fields describing the name of the patient and supervising clinician; numbers associated with the patient's bed, room, and body-worn monitor; and the type of alarm generated from the patient. Graphical icons, similar to those shown in FIG. 9, indicate the patient's activity level. Additional icons show the body-worn monitor's battery power, wireless signal strength, and whether or not an alarm has been generated. Each area 108 also clearly indicates numerical values for each vital sign measured continuously by the body-worn monitor. The monitor displaying the patient view 106 typically includes a touch-panel. Tapping on the patient-specific area 108 generates a new view (not shown in the figure) that expands all the information in the area 108, and additionally shows time-dependent waveforms (similar to those shown in FIGS. 2-5) corresponding to the patient.

FIG. 10B shows a map view 107 that indicates the location and activity state of each patient in the hospital area. Each patient's location is typically determined by processing the wireless signal from their body-worn monitor (e.g., by triangulating on signals received by neighboring 802.11 base stations, or simply using proximity to the base station) or by using more advanced methods (e.g. time-of-flight analysis of the wireless signal, or conventional or network-assisted GPS), both of which are done using techniques known in the art. The patient's location is mapped to a grid representing the distribution of beds in the hospital area to generate the map view 107. The map view 107 typically refreshes every 10-20 seconds, showing an updated location and activity state for each patient.

Figure 11A:
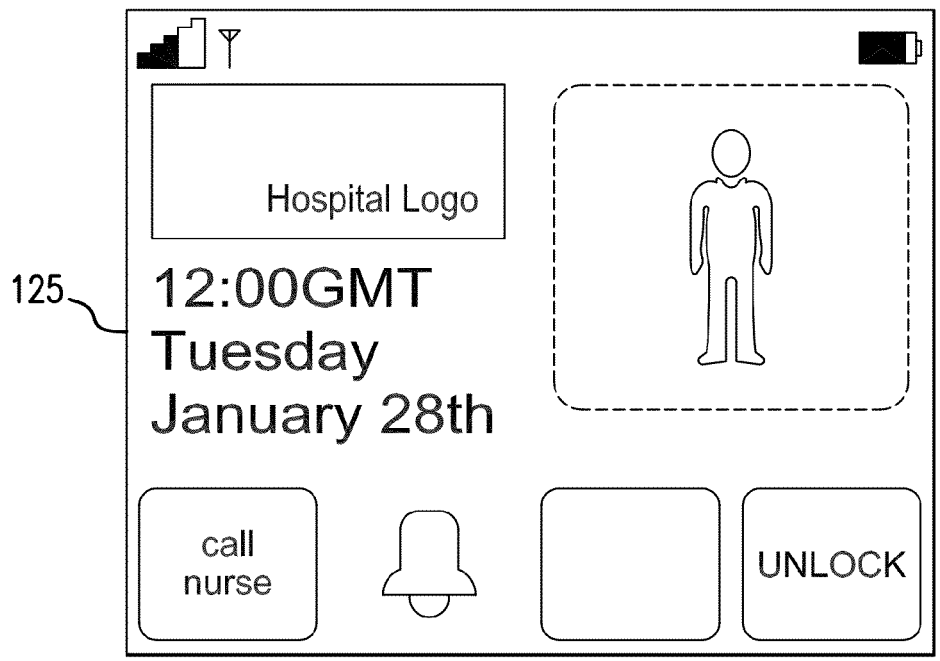
FIGS. 11A and 11B show, respectively, patient and medical professional views used in the GUI rendered on the body-worn monitor.
Figure 11B:
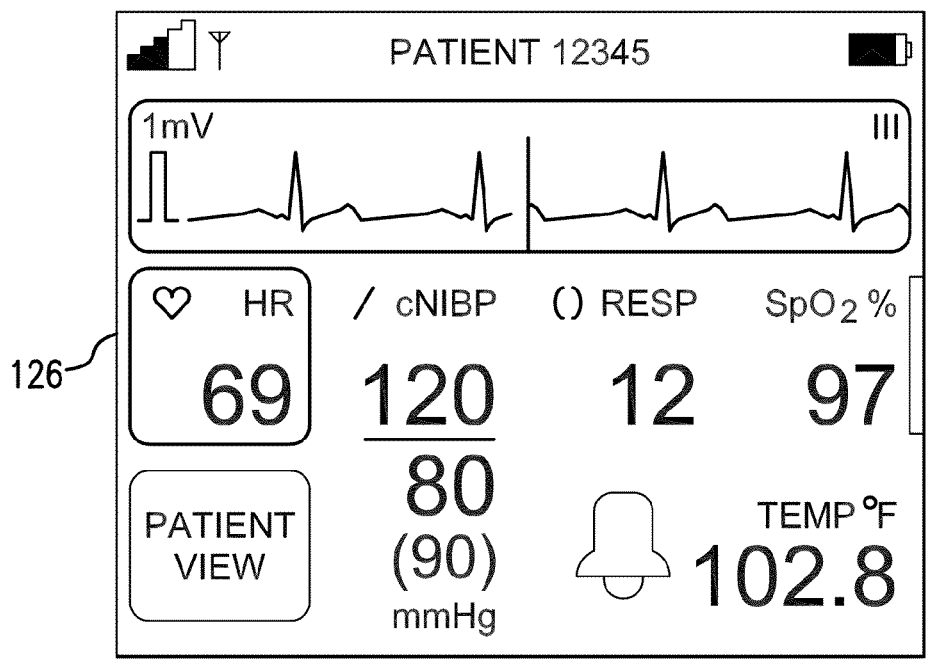

FIGS. 11A and 11B show GUIs rendered by a display screen directly on the body-worn monitor. The GUIs feature screens 125, 126 that are designed for the patient (125 in FIG. 11A) and medical professional (126 in FIG. 11B). The patient view 125 purposefully lacks any content related to vital signs, and instead is designed to be relatively generic, featuring the time, date, and icons indicating the patient's activity level, whether or not an alarm has been generated, battery life, and wireless signal strength. The display screen is a touch panel, and features a graphical 'call nurse' button that, once depressed, sends a signal to the central nursing station indicating that the patient needs assistance from a nurse. The patient view 125 includes a button labeled 'UNLOCK' that, once activated, allows a nurse or doctor to activate the medical professional view 126 shown in FIG. 11B. Tapping the UNLOCK button powers an infrared barcode scanner in the body-worn monitor; this scans a barcode printed on a badge of the nurse of doctor and compares an encoded identifier to a database stored in an internal memory. A match prompts the monitor to render the medical professional view 126, shown in FIG. 11B.

The medical professional view 126 is designed to have a look and feel similar to each area 108 shown in FIG. 10A. This makes it relatively easy for the nurse to interpret information rendered on both the body-worn monitor and remote monitor. The view 126 features fields for a patient identifier, numerical values for vital signs, a time-dependent ECG waveform with a span of approximately 5 seconds, and icons indicating battery life, wireless signal strength, and whether or not an alarm has been generated. A fixed bar proximal to the ECG waveform indicates a signal strength of 1 mV, as required by the AAMI:ANSI EC13 specification for cardiac monitors. Depressing the 'PATIENT VIEW' button causes the GUI to revert back to the patient view 125 shown in FIG. 11A.

Algorithms for Determining Patient Motion, Posture, Arm Height, Activity Level and the Effect of these Properties on Blood Pressure Described below is an algorithm for using the three accelerometers featured in the above-described body-worn monitor to calculate a patient's motion, posture, arm height, activity level. Each of these parameters affects both blood pressure and PTT, and thus inclusion of them in an algorithm can improve the accuracy of these measurements, and consequently reduce false alarms/alerts associated with them.

Calculating Arm Height

Figure 12:
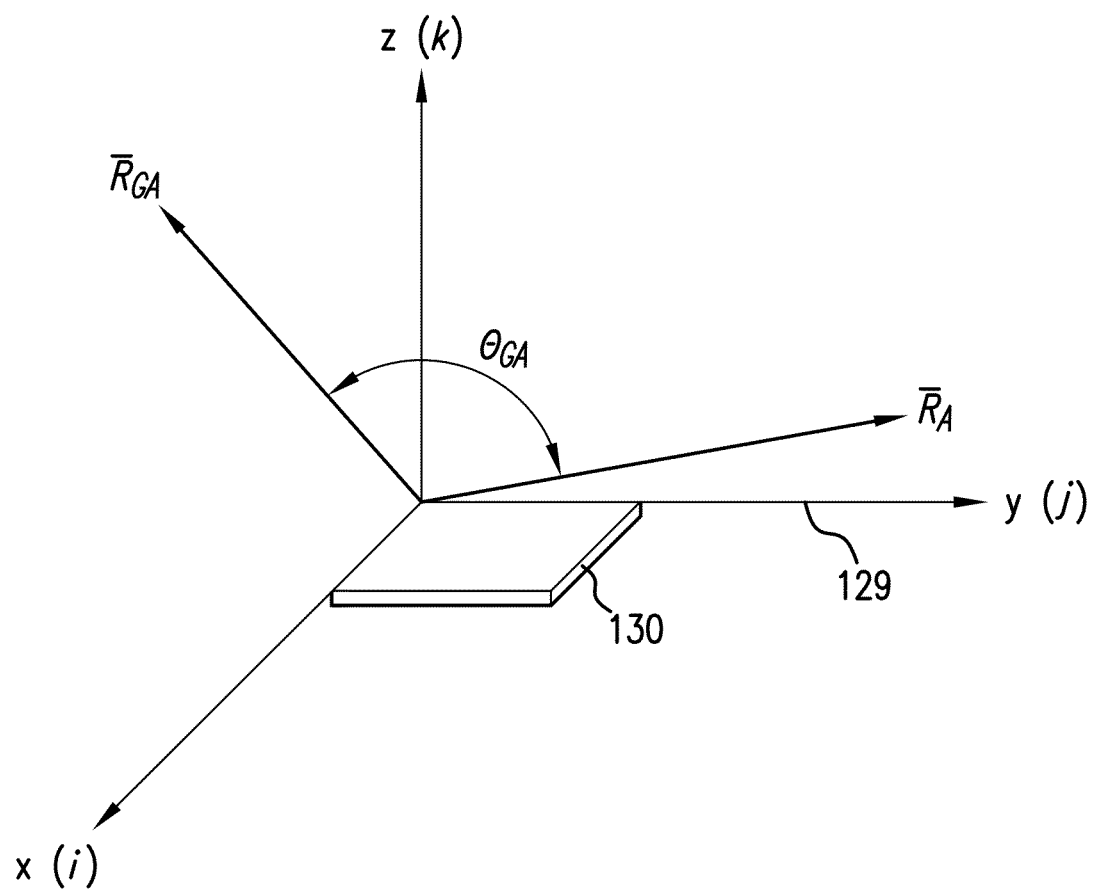
FIG. 12 shows a schematic drawing of a coordinate system used to calibrate accelerometers used in the body-worn monitor of FIG. 1.

To calculate a patient's arm height it is necessary to build a mathematical model representing the geometric orientation of the patient's arm, as detected with signals from the three accelerometers. FIG. 12 shows a schematic image of a coordinate system 129 centered around a plane 130 used to build this model for determining patient motion and activity level, and arm height. Each of these parameters, as discussed in detail below, has an impact on the patient's vital signs, and particularly blood pressure.

The algorithm for estimating a patient's motion and activity level begins with a calculation to determine their arm height. This is done using signals from accelerometers attached to the patient's bicep (i.e., with reference to FIG. 20A, an accelerometer included in the bulkhead portion 296 of cable 286) and wrist (i.e. the accelerometer surface-mounted to a circuit board within the wrist-worn transceiver 272). The mathematical model used for this algorithm features a calibration procedure used to identify the alignment of an axis associated with a vector $R_A$, which extends along the patient's arm. Typically this is done by assuming the body-worn monitor is attached to the patient's arm in a manner consistent with that that shown in FIGS. 20A, B, and by using preprogrammed constants stored in memory associated with the CPU. Alternatively this can be done by prompting the patient (using, e.g., the wrist-worn transceiver) to assume a known and consistent position with respect to gravity (e.g., hanging their arm down in a vertical configuration). The axis of their arm is determined by sampling a DC portion of time-dependent ACC waveforms along the x, y, and z axes associated with the two above-mentioned accelerometers (i.e. $ACC_{1-6}$; the resultant values have units of g's) during the calibration procedure, and storing these numerical values as a vector in memory accessible with the CPU within the wrist-worn transceiver.

The algorithm determines a gravitational vector $R_{GA}$ at a later time by again sampling DC portions of $ACC_{1-6}$. Once this is complete, the algorithm determines the angle$_{GA}$ between the fixed arm vector $R_A$ and the gravitational vector $R_{GA}$ by calculating a dot product of the two vectors. As the patient moves their arm, signals measured by the two accelerometers vary, and are analyzed to determine a change in the gravitational vector $R_{GA}$ and, subsequently, a change in the angle$_{GA}$. The angle$_{GA}$ can then be combined with an assumed, approximate length of the patient's arm (typically 0.8 m) to determine its height relative to a proximal joint, e.g. the elbow.

Figure 13:
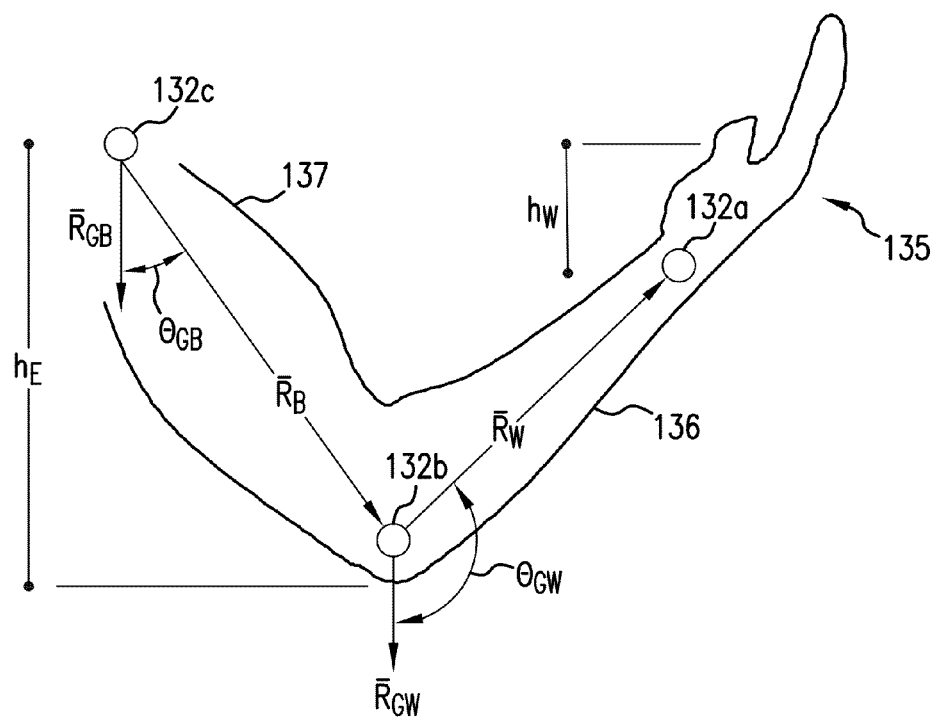
FIG. 13 shows a schematic drawing of three accelerometers attached to a patient's arm and connected to the body-worn monitor of FIG. 1.

FIG. 13 indicates how this model and approach can be extended to determine the relative heights of the upper 137 and lower 136 segments of a patient's arm 135. In this derivation, described below, i, j, k represent the vector directions of, respectively, the x, y, and z axes of the coordinate system 129 shown in FIG. 12. Three accelerometers 132a-c are disposed, respectively, on the patient's chest just above their armpit, near their bicep, and near their wrist; this is consistent with positioning within the body-worn monitor, as described in FIGS. 20A,B. The vector $R_B$ extending along the upper portion 137 of the patient's arm is defined in this coordinate system as:

$$\vec{R}_B = r_{Bx}\hat{i} + r_{By}\hat{j} + r_{Bz}\hat{k} \tag{1}$$

At any given time, the gravitational vector $R_{GB}$ is determined from ACC waveforms ($ACC_{1-3}$) using signals from the accelerometer 132b located near the patient's bicep, and is represented by equation (2) below:

$$\vec{R}_{GB}[n] = y_{Bx}[n]\hat{i} + y_{By}[n]\hat{j} + y_{Bz}[n]\hat{k} \tag{2}$$

Specifically, the CPU in the wrist-worn transceiver receives digitized signals representing the DC portion of the $ACC_{1-3}$ signals measured with accelerometer 132b, as represented by equation (3) below, where the parameter n is the value (having units of g's) sampled directly from the DC portion of the ACC waveform:

$$y_{Bx}[n] = y_{DC,Bicep,x}[n]; \ y_{By}[n] = y_{DC,Bicep,y}[n]; \\ y_{Bz}[n] = y_{DC,Bicep,z}[n] \tag{3}$$

The cosine of the angle$_{GB}$ separating the vector $R_B$ and the gravitational vector $R_{GB}$ is determined using equation (4):

$$\cos(\theta_{GB}[n]) = \frac{\vec{R}_{GB}[n] \cdot \vec{R}_B}{\|\vec{R}_{GB}[n]\| \|\vec{R}_B\|} \tag{4}$$

The definition of the dot product of the two vectors $R_B$ and $R_{GB}$ is:

$$\vec{R}_{GB}[n] \cdot \vec{R}_B = (y_{Bx}[n] \times r_{Bx}) + (y_{By}[n] \times r_{By}) + (y_{Bz}[n] \times r_{Bz}) \tag{5}$$

and the definitions of the norms or magnitude of the vectors $R_B$ and $R_{GB}$ are:

$$\|\vec{R}_{GB}[n]\| = \sqrt{(y_{Bx}[n])^2 + (y_{By}[n])^2 + (y_{Bz}[n])^2} \tag{6}$$

and $$\|\vec{R}_B\| = \sqrt{(r_{Bx})^2 + (r_{By})^2 + (r_{Bz})^2} \tag{7}$$

Using the norm values for these vectors and the angle$_{GB}$ separating them, as defined in equation (4), the height of the patient's elbow relative to their shoulder joint, as characterized by the accelerometer on their chest ($h_E$), is determined using equation (8), where the length of the upper arm is estimated as $L_B$:

$$h_E[n] = -L_B \times \cos(\theta_{GB}[n]) \tag{8}$$

As is described in more detail below, equation (8) estimates the height of the patient's arm relative to their heart. And this, in turn, can be used to further improve the accuracy of PTT-based blood pressure measurements.

The height of the patient's wrist joint $h_W$ is calculated in a similar manner using DC components from the time-domain waveforms ($ACC_{4-6}$) collected from the accelerometer 132a mounted within the wrist-worn transceiver. Specifically, the wrist vector $R_W$ is given by equation (9):

$$\vec{R}_W = r_{Wx}\hat{i} + r_{Wy}\hat{j} + r_{Wz}\hat{k} \tag{9}$$

and the corresponding gravitational vector $R_{GW}$ is given by equation (10):

$$\vec{R}_{GW}[n] = y_{Wx}[n]\hat{i} + y_{Wy}[n]\hat{j} + y_{Wz}[n]\hat{k} \tag{10}$$

The specific values used in equation (10) are measured directly from the accelerometer 132a; they are represented as n and have units of g's, as defined below:

$$y_{Wx}[n] = y_{DC,Wrist,x}[n]; \ y_{Wy}[n] = y_{DC,Wrist,y}[n]; \\ y_{Wz}[n] = y_{DC,Wrist,z}[n] \tag{11}$$

The vectors $R_W$ and $R_{GW}$ described above are used to determine the cosine of the angle$_{GW}$ separating them using equation (12):

$$\cos(\theta_{GW}[n]) = \frac{\vec{R}_{GW}[n] \cdot \vec{R}_W}{\|\vec{R}_{WB}[n]\| \|\vec{R}_W\|} \tag{12}$$

The definition of the dot product between the vectors $R_W$ and $R_{GW}$ is:

$$\vec{R}_{GW}[n] \cdot \vec{R}_W = (y_{Wx}[n] \times r_{Wx}) + (y_{Wy}[n] \times r_{Wy}) + (y_{Wz}[n] \times r_{Wz}) \tag{13}$$

and the definitions of the norm or magnitude of both the vectors $R_W$ and $R_{GW}$ are:

$$\|\vec{R}_{Gw}[n]\| = \sqrt{(y_{Wx})[n])^2 + r_{Wy}[n])^2 + (y_{Wz}[n])^2} \tag{14}$$

and $$\|\vec{R}_W\| = \sqrt{(r_{Wx})^2 + (r_{Wy})^2 + (r_{Wz})^2} \tag{15}$$

The height of the patient's wrist $h_W$ can be calculated using the norm values described above in equations (14) and (15), the cosine value described in equation (12), and the height of the patient's elbow determined in equation (8):

$$h_W[n] = h_E[n] - L_W \times \cos(\theta_{GW}[n]) \tag{16}$$

In summary, the algorithm can use digitized signals from the accelerometers mounted on the patient's bicep and wrist, along with equations (8) and (16), to accurately determine the patient's arm height and position. As described below, these parameters can then be used to correct the PTT and provide a blood pressure calibration, similar to the cuff-based indexing measurement described above, that can further improve the accuracy of this measurement.

Calculating the Influence of Arm Height on Blood Pressure

A patient's blood pressure, as measured near the brachial artery, will vary with their arm height due to hydrostatic forces and gravity. This relationship between arm height and blood pressure enables two measurements: 1) a blood pressure 'correction factor', determined from slight changes in the patient's arm height, can be calculated and used to improve accuracy of the base blood pressure measurement; and 2) the relationship between PTT and blood pressure can be determined (like it is currently done using the indexing measurement) by measuring PTT at different arm heights, and calculating the change in PTT corresponding to the resultant change in height-dependent blood pressure. Specifically, using equations (8) and (16) above, and (21) below, an algorithm can calculate a change in a patient's blood pressure (BP) simply by using data from two accelerometers disposed on the wrist and bicep. The BP can be used as the correction factor. Exact blood pressure values can be estimated directly from arm height using an initial blood pressure value (determined, e.g., using the cuff-based module during an initial indexing measurement), the relative change in arm height, and the correction factor. This measurement can be performed, for example, when the patient is first admitted to the hospital. PTT determined at different arm heights provides multiple data points, each corresponding to a unique pair of blood pressure values determined as described above. The change in PTT values (PTT) corresponds to changes in arm height.

From these data, the algorithm can calculate for each patient how blood pressure changes with PTT, i.e. BP/PTT. This relationship relates to features of the patient's cardiovascular system, and will evolve over time due to changes, e.g., in the patient's arterial tone and vascular compliance. Accuracy of the body-worn monitor's blood pressure measurement can therefore be improved by periodically calculating BP/PTT. This is best done by: 1) combining a cuff-based initial indexing measurement to set baseline values for SYS, DIA, and MAP, and then determining BP/PTT as described above; and 2) continually calculating BP/PTT by using the patient's natural motion, or alternatively using well-defined motions (e.g., raising and lower the arm to specific positions) as prompted at specific times by monitor's user interface.

Going forward, the body-worn monitor measures PTT, and can use this value and the relationship determined from the above-described calibration to convert this to blood pressure. All future indexing measurements can be performed on command (e.g., using audio or visual instructions delivered by the wrist-worn transceiver) using changes in arm height, or as the patient naturally raises and lowers their arm as they move about the hospital.

To determine the relationship between PTT, arm height, and blood pressure, the algorithm running on the wrist-worn transceiver is derived from a standard linear model shown in equation (17):

$$PTT = \left(\frac{1}{m_{BP}}\right) \times P_{MAP} + \tilde{B} \quad (17)$$

Assuming a constant velocity of the arterial pulse along an arterial pathway (e.g., the pathway extending from the heart, through the arm, to the base of the thumb):

$$\frac{\partial(PWV)}{\partial r} = 0 \quad (18)$$

the linear PTT model described in equation (17) becomes:

$$\frac{\partial(PTT)}{\partial r} = \left(\frac{1}{L}\right)\left(\frac{1}{m_{BP}} \times MAP + \tilde{B}\right) \quad (19)$$

Equation (19) can be solved using piecewise integration along the upper 137 and lower 136 segments of the arm to yield the following equation for height-dependent PTT:

$$PTT = \quad (20)$$

$$\left(\frac{1}{m_{BP}} \times MAP + B\right) - \frac{1}{m_{BP}} \times \left[\left(\frac{L_1}{L}\right)\left(\frac{\rho G h_E}{2}\right) + \left(\frac{L_2}{L}\right)\left(\frac{\rho G}{2}(h_W + h_E)\right)\right]$$

From equation (20) it is possible to determine a relative pressure change $P_{rel}$ induced in a cNIBP measurement using the height of the patient's wrist ($h_W$) and elbow ($h_E$):

$$P_{rel}[n] = \left(\frac{L_1}{L}\right)\left(\frac{\rho G h_E[n]}{2}\right) + \left(\frac{L_2}{L}\right)\left(\frac{\rho G}{2}(h_W[n] + h_E[n])\right) \quad (21)$$

As described above, $P_{rel}$ can be used to both calibrate the cNIBP measurement deployed by the body-worn monitor, or supply a height-dependent correction factor that reduces or eliminates the effect of posture and arm height on a PTT-based blood pressure measurement.

Figure 14:
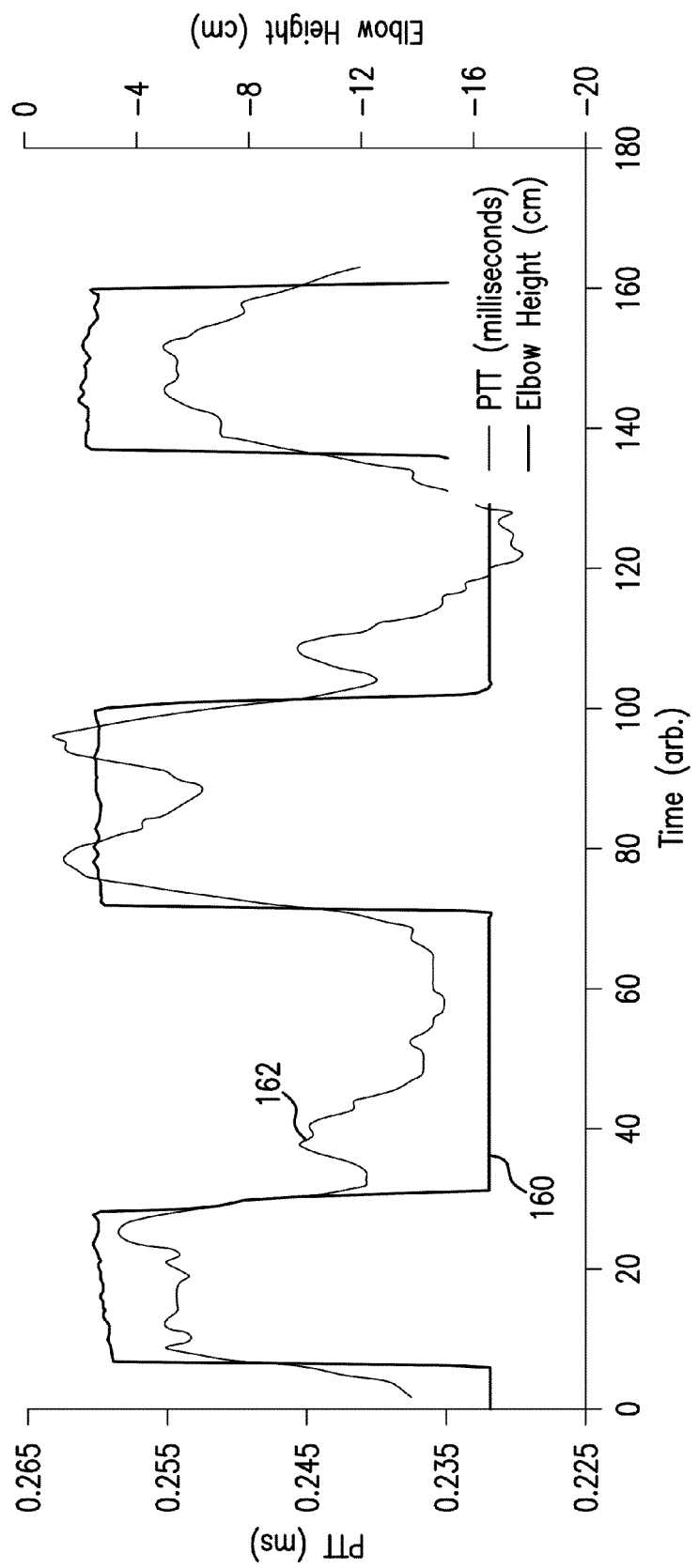
FIG. 14 is a graph of time-dependent waveforms indicating a patient's elbow height and corresponding PTT.

FIG. 14 shows actual experimental data that illustrate how PTT changes with arm height. Data for this experiment were collected as the subject periodically raised and lowered their arm using a body-worn monitor similar to that shown in FIGS. 20A and 20B. Such motion would occur, for example, if the patient was walking. As shown in FIG. 14, changes in the patient's elbow height are represented by time-dependent changes in the DC portion of an ACC waveform, indicated by trace 160. These data are measured directly from an accelerometer positioned near the patient's bicep, as described above. PTT is measured from the same arm using the PPG and ECG waveforms, and is indicated by trace 162. As the patient raises and lowers their arm their PTT rises and falls accordingly, albeit with some delay due to the reaction time of the patient's cardiovascular system.

Calculating a Patient's Posture

Figure 15:
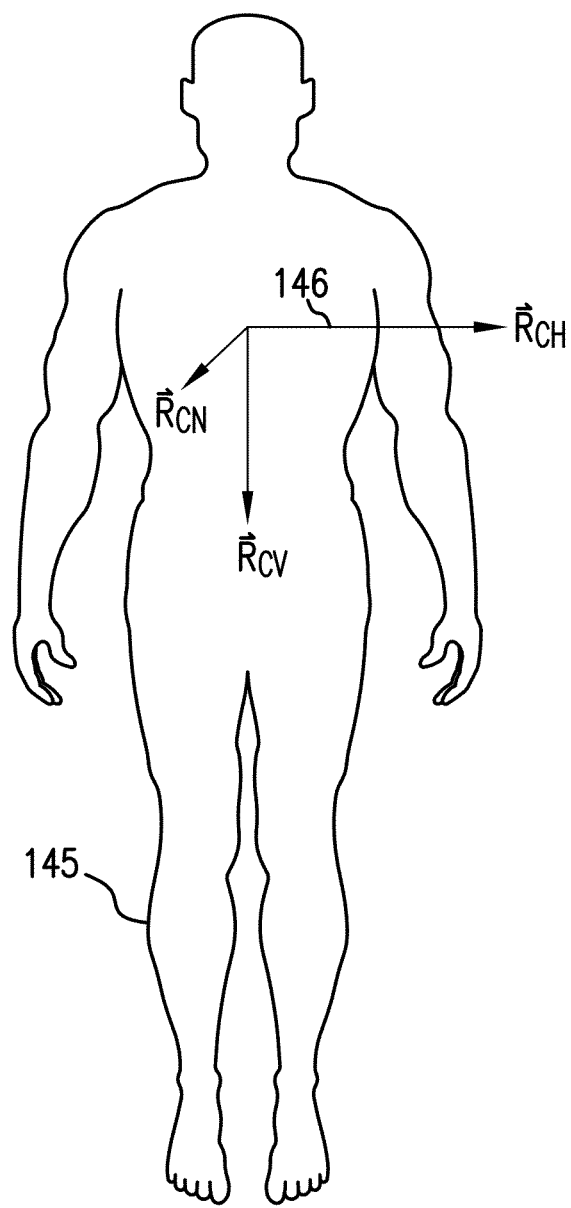
FIG. 15 shows a schematic drawing of a coordinate system representing an accelerometer coordinate space superimposed on a patient's torso.

As described above in Tables 1A-C, a patient's posture can influence how the above-described system generates alarms/alerts. The body-worn monitor can determine a patient's posture using time-dependent ACC waveforms continuously generated from the three patient-worn accelerometers, as shown in FIGS. 20A, B. In embodiments, the accelerometer worn on the patient's chest can be exclusively used to simplify this calculation. An algorithm operating on the wrist-worn transceiver extracts DC values from waveforms measured from this accelerometer and processes them with an algorithm described below to determine posture. Specifically, referring to FIG. 15, torso posture is determined for a patient 145 using angles determined between the measured gravitational vector and the axes of a torso coordinate space 146. The axes of this space 146 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in this procedure is to identify alignment of $\vec{R}_{CV}$ in the chest accelerometer coordinate space. This can be determined in either of two approaches. In the first approach, $\vec{R}_{CV}$ is assumed based on a typical alignment of the body-worn monitor relative to the patient. During manufacturing, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the display, or audio instructions transmitted through the speaker) to assume a known position with respect to gravity (e.g., standing up with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not the orthogonal to the gravity vector.

The second step in the procedure is to identify the alignment of $\vec{R}_{CN}$ in the chest accelerometer coordinate space. The monitor can determine this vector, similar to the way it determines $\vec{R}_{CV}$, with one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CN}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

Figure 16:
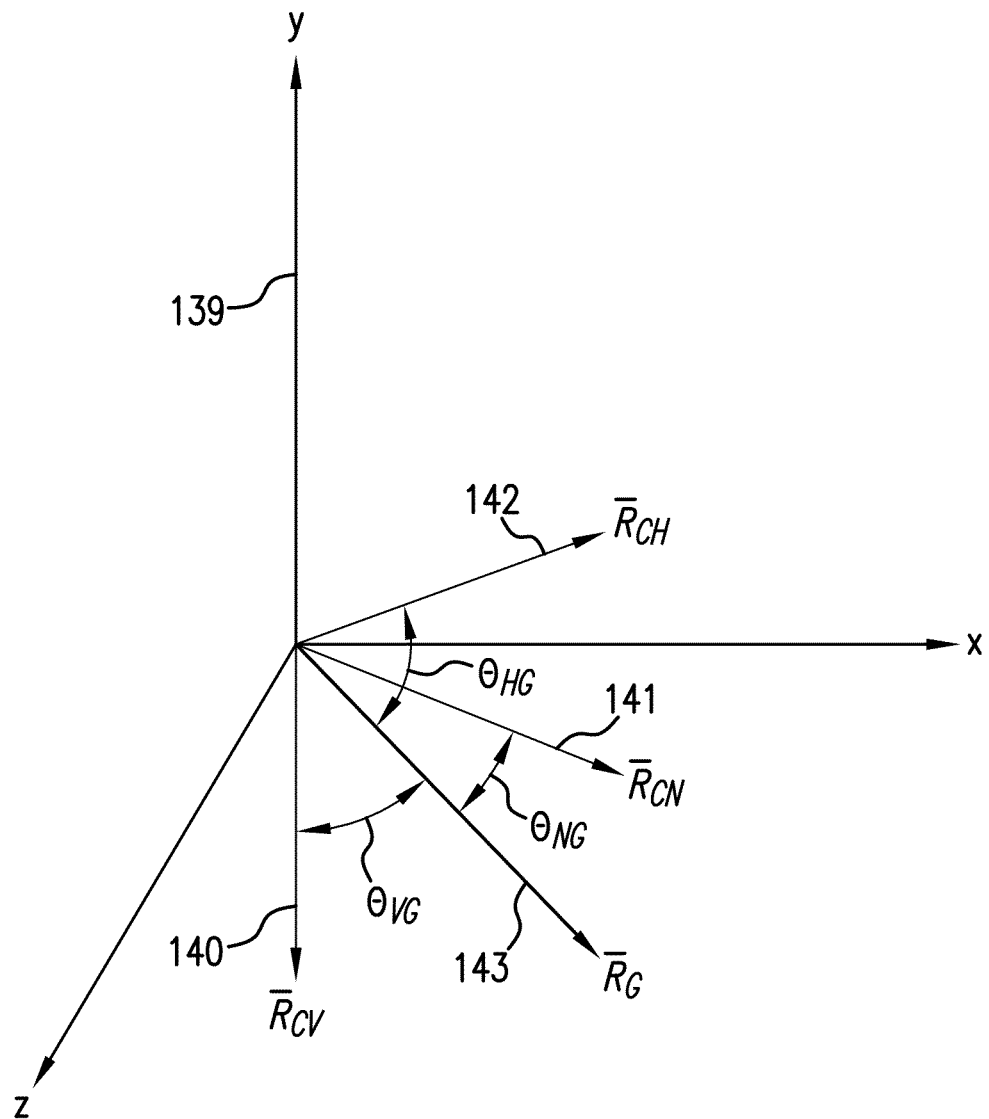
FIG. 16 shows the accelerometer coordinate space of FIG. 15 and a vector representing the direction and magnitude of gravity, along with angles separating the vector from each axis of the coordinate system.

FIG. 16 shows the geometrical relationship between $\vec{R}_{CV}$ 140, $\vec{R}_{CN}$ 141, and $\vec{R}_{CH}$ 142 and a gravitational vector $\vec{R}_G$ 143 measured from a moving patient in a chest accelerometer coordinate space 139. The body-worn monitor continually determines a patient's posture from the angles separating these vectors. Specifically, the monitor continually calculates $\vec{R}_G$ 143 for the patient using DC values from the ACC waveform measured by the chest accelerometer. From this vector, the body-worn monitor identifies angles ($\theta_{VG}$, $\theta_{NG}$, and $\theta_{HG}$) separating it from $\vec{R}_{CV}$ 140, $\vec{R}_{CN}$ 141, and $\vec{R}_{CH}$ 142. The body-worn monitor then compares these three angles to a set of predetermine posture thresholds to classify the patient's posture.

The derivation of this algorithm is as follows. Based on either an assumed orientation or a patient-specific calibration procedure described above, the alignment of $\vec{R}_{CV}$ in the chest accelerometer coordinate space is given by:

$$\vec{R}_{CV} = r_{CVx}\hat{i} + r_{CVy}\hat{j} + r_{CVz}\hat{k} \quad (22)$$

At any given moment, $\vec{R}_G$ is constructed from DC values of the ACC waveform from the chest accelerometer along the x, y, and z axes:

$$\vec{R}_G[n] = y_{Cx}[n]\hat{i} + y_{Cy}[n]\hat{j} + y_{Cz}[n]\hat{k} \quad (23)$$

Equation (24) shows specific components of the ACC waveform used for this calculation:

$$y_{Cx}[n] = y_{DC,chest,x}[n]; y_{Cy}[n] = y_{DC,chest,y}[n];$$
$$y_{Cz}[n] = y_{DC,chest,z}[n] \quad (24)$$

The angle between $\vec{R}_{CV}$ and $\vec{R}_G$ is given by equation (25):

$$\theta_{VG}[n] = \arccos\left(\frac{\vec{R}_G[n] \cdot \vec{R}_{CV}}{\|\vec{R}_G[n]\|\|\vec{R}_{CV}\|}\right) \quad (25)$$

where the dot product of the two vectors is defined as:

$$\vec{R}_G[n] \cdot$$
$$\vec{R}_{CV} = (y_{Cx}[n] \times r_{CVx}) + (y_{Cy}[n] \times r_{CVy}) + (y_{Cz}[n] \times r_{CVz}) \quad (26)$$

The definition of the norms of $\vec{R}_G$ and $\vec{R}_{CV}$ are given by equations (27) and (28):

$$\|\vec{R}_G[n]\| = \sqrt{(y_{Cx}[n])^2 + (y_{Cy}[n])^2 (y_{Cz}[n])^2} \quad (27)$$

$$\|\vec{R}_{CV}\| = \sqrt{(r_{CVx})^2 + (r_{CVy})^2 + (r_{CVz})^2} \quad (28)$$

As shown in equation (29), the monitor compares the vertical angle $\theta_{VG}$ to a threshold angle to determine whether the patient is vertical (i.e. standing upright) or lying down:

$$\text{if } \theta_{VG} \leq 45° \text{ then Torso State=0, the patient is upright} \quad (29)$$

If the condition in equation (29) is met the patient is assumed to be upright, and their torso state, which is a numerical value equated to the patient's posture, is equal to 0. The torso state is processed by the body-worn monitor to indicate, e.g., a specific icon corresponding to this state, such as icon 105a in FIG. 9. The patient is assumed to be lying down if the condition in equation (8) is not met, i.e. $\theta_{VG}$>45 degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by equation (30), where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \quad (30)$$

The angle between $\vec{R}_{CN}$ and $\vec{R}_G$ determined from DC values extracted from the chest accelerometer ACC waveform is given by equation (31):

$$\theta_{NG}[n] = \arccos\left(\frac{\vec{R}_G[n] \cdot \vec{R}_{CN}}{\|\vec{R}_G[n]\|\|\vec{R}_{CN}\|}\right) \quad (31)$$

The body-worn monitor determines the normal angle $\theta_{NG}$ and then compares it to a set of predetermined threshold angles to determine which position the patient is lying in, as shown in equation (32):

if $\theta_{NG} \leq 35°$ then Torso State=1, the patient is supine if $\theta_{NG} \geq 135°$ then Torso State=2, the patient is prone  (32)

Icons corresponding to these torso states are shown, for example, as icons 105h and 105g in FIG. 9. If the conditions in equation (32) are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by equation (33), where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CV_3}\hat{i} + r_{CV_3}\hat{j} + r_{CV_2}\hat{k} = \hat{R}_{CV} \times \vec{R}_{CN} \quad (33)$$

The angle $\theta_{HG}$ between $\vec{R}_{CH}$ and $\vec{R}_G$ is determined using equation (34):

$$\theta_{HG}[n] = \arccos\left(\frac{\vec{R}_G[n] \cdot \vec{R}_{CH}}{\|\vec{R}_G[n]\|\|\vec{R}_{CH}\|}\right) \quad (34)$$

The monitor compares this angle to a set of predetermined threshold angles to determine if the patient is lying on their right or left side, as given by equation (35):

if $\theta_{HG} \geq 90°$ then Torso State=3, the patient is on their right side if $\theta_{NG} < 90°$ then Torso State=4, the patient is on their left side  (35)

Table 4 describes each of the above-described postures, along with a corresponding numerical torso state used to render, e.g., a particular icon:

TABLE 4 postures and their corresponding torso states

| Posture | Torso State |
| --- | --- |
| Upright | 0 |
| supine: lying on back | 1 |
| prone: lying on chest | 2 |
| lying on right side | 3 |
| lying on left side | 4 |
| undetermined posture | 5 |

Figure 17A:
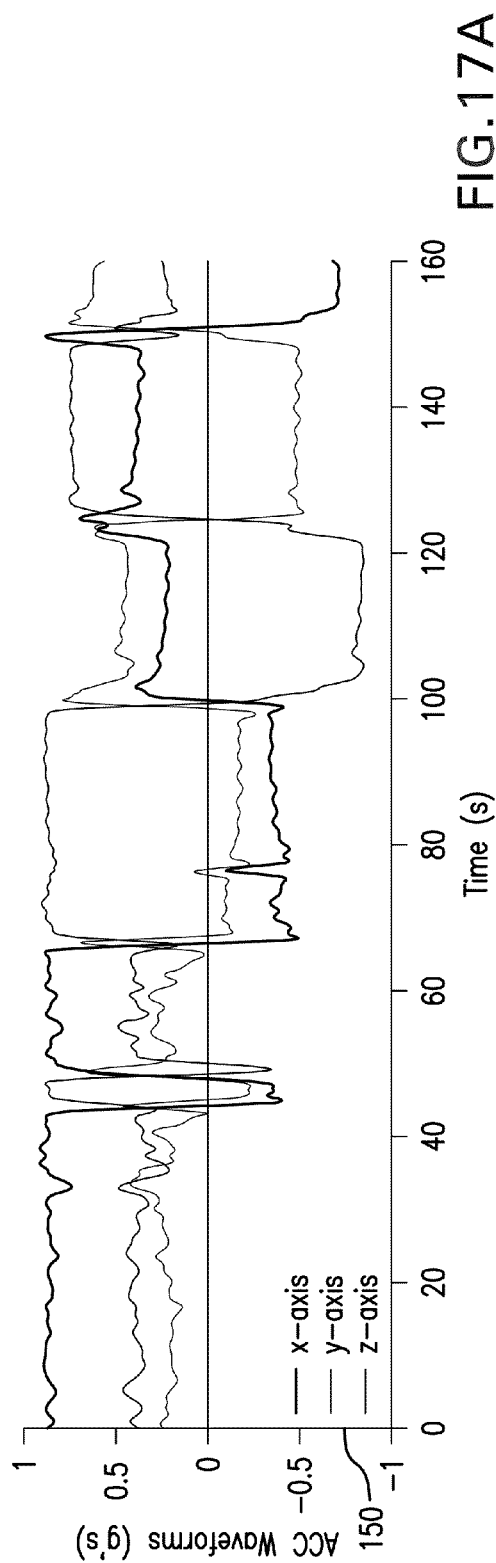
FIG. 17A is a graph showing time-dependent motion waveforms corresponding to different posture states and measured with an accelerometer positioned on a patient's chest.
Figure 17B:
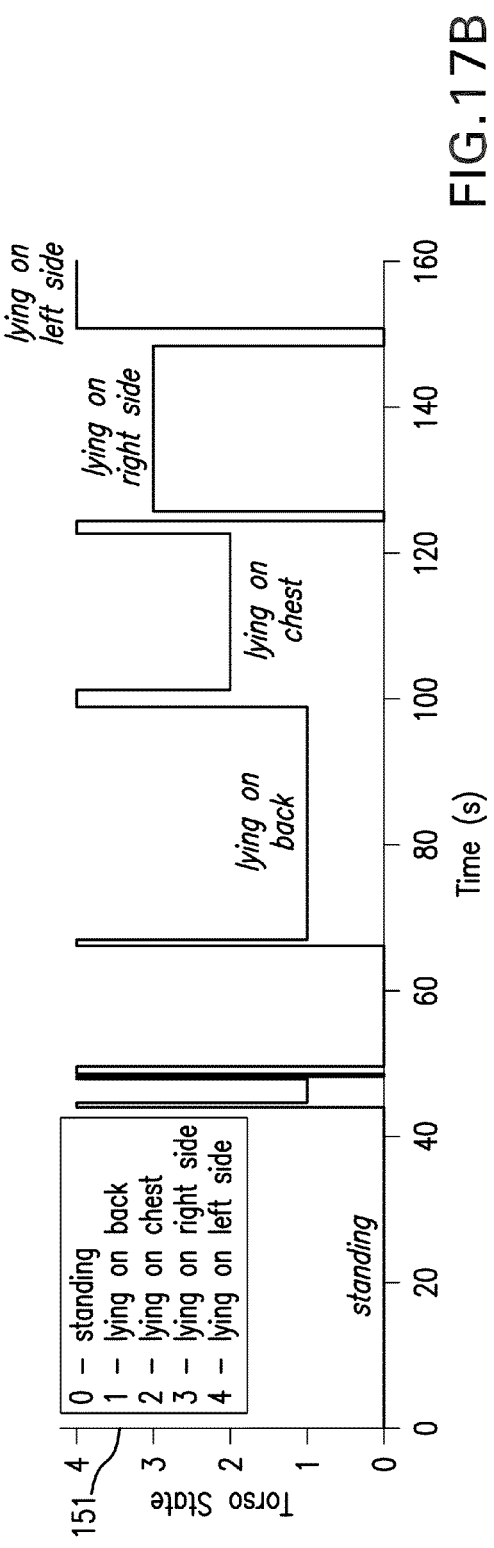
FIG. 17B is a graph showing posture states calculated using the time-dependent motion waveforms of FIG. 17A and a mathematical model for determining a patient's posture.

FIGS. 17A and 17B show, respectively, graphs of time-dependent ACC waveforms 150 measured along the x, y, and z-axes, and the torso states (i.e. postures) 151 determined from these waveforms for a moving patient. As the patient moves, the DC values of the ACC waveforms measured by the chest accelerometer vary accordingly, as shown by the graph 150 in FIG. 17A. The body-worn monitor processes these values as described above to continually determine $\vec{R}_G$ and the various quantized torso states for the patient, as shown in the graph 151 in FIG. 17B. The torso states yield the patient's posture as defined in Table 4. For this study the patient rapidly alternated between standing, lying on their back, chest, right side, and left side within about 150 seconds. As described above, different alarm/alert conditions (e.g. threshold values) for vital signs can be assigned to each of these postures, or the specific posture itself may result in an alarm/alert. Additionally, the time-dependent properties of the graph 151 can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

Calculating a Patient's Activity

An algorithm can process information generated by the accelerometers described above to determine a patient's specific activity (e.g., walking, resting, convulsing), which is then used to reduce the occurrence of false alarms. This classification is done using a 'logistic regression model classifier', which is a type of classifier that processes continuous data values and maps them to an output that lies on the interval between 0 and 1. A classification 'threshold' is then set as a fractional value within this interval. If the model output is greater than or equal to this threshold, the classification is declared 'true', and a specific activity state can be assumed for the patient. If the model output falls below the threshold, then the specific activity is assumed not to take place.

This type of classification model offers several advantages. First, it provides the ability to combine multiple input variables into a single model, and map them to a single probability ranging between 0 and 1. Second, the threshold that allows the maximum true positive outcomes and the minimum false positive outcomes can be easily determined from a ROC curve, which in turn can be determined using empirical experimentation and data. Third, this technique requires minimal computation.

The formula for the logistic regression model is given by equation (36) and is used to determine the outcome, P, for a set of buffered data:

$$P = \frac{1}{1 - \exp(-z)} \quad (36)$$

The logit variable z is defined in terms of a series of predictors ($x_i$), each affected by a specific type of activity, and determined by the three accelerometers worn by the patient, as shown in equation (37):

$$z = b_0 + b_1 x_1 + b_2 x_2 + \ldots + b_m x_m \quad (37)$$

In this model, the regression coefficients ($b_i$, i=0, 1, ..., m) and the threshold ($P_{th}$) used in the patient motion classifier and signal corruption classifiers are determined empirically from data collected on actual subjects. The classifier results in a positive outcome as given in equation (38) if the logistic model output, P, is greater than the predetermined threshold, $P_{th}$:

If $P \geq P_{th}$ then Classifier State=1  (38)

Figure 18:
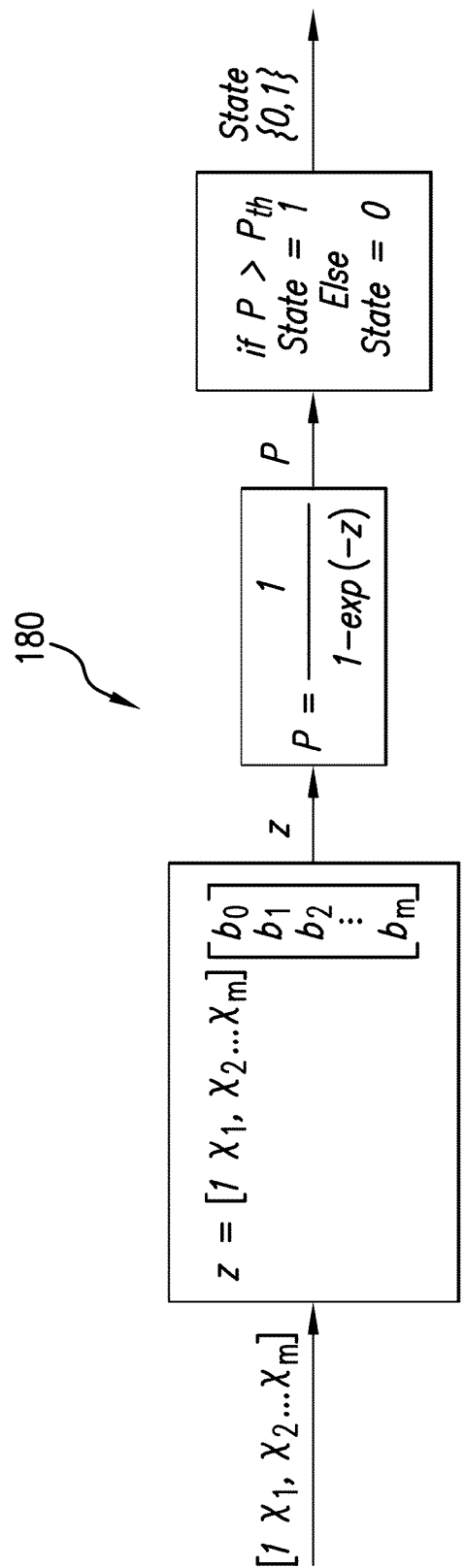
FIG. 18 is a schematic drawing of a calculation used to determine a type of activity exhibited by a patient.

FIG. 18 shows a block diagram 180 indicating the mathematical model used to determine the above-described logistic regression model classifier. In this model, the series of predictor variables ($x_1$) are determined from statistical properties of the time-dependent ACC waveforms, along with specific frequency components contained in the power spectra of these waveforms. The frequency components are determined in a low-frequency region (0-20 Hz) of these spectra that corresponds to human motion, and are shown, for example, by the series of bars 81 in FIG. 7. Specifically, the predictor variables can be categorized by first taking a power spectrum of a time-dependent ACC waveform generated by an accelerometer, normalizing it, and then separating the fractional power into frequency bands according to Table 5, below:

TABLE 5 predictor variables and their relationship to the accelerometer signal

| predictor variable | Description |
|---|---|
| $x_1$ | normalized power of the AC component of the time-dependent accelerometer signal |
| $x_2$ | average arm angle measured while time-dependent accelerometer signal is collected |
| $x_3$ | standard deviation of the arm angle while time-dependent accelerometer signal is collected |
| $x_4$ | fractional power of the AC component of the frequency-dependent accelerometer signal between 0.5-1.0 Hz |
| $x_5$ | fractional power of the AC component of the frequency-dependent accelerometer signal between 1.0-2.0 Hz |
| $x_6$ | fractional power of the AC component of the frequency-dependent accelerometer signal between 2.0-3.0 Hz |
| $x_7$ | fractional power of the AC component of the frequency-dependent accelerometer signal between 3.0-4.0 Hz |
| $x_8$ | fractional power of the AC component of the frequency-dependent accelerometer signal between 4.0-5.0 Hz |
| $x_9$ | fractional power of the AC component of the frequency-dependent accelerometer signal between 5.0-6.0 Hz |
| $x_{10}$ | fractional power of the AC component of the frequency-dependent accelerometer signal between 6.0-7.0 Hz |

The predictor variables described in Table 5 are typically determined from ACC signals generated by accelerometers deployed in locations that are most affected by patient motion. Such accelerometers are typically mounted directly on the wrist-worn transceiver, and on the bulkhead connector attached to the patient's arm. The normalized signal power ($x_1$) for the AC components ($y_{W,i}$, i=x, y, z) calculated from the ACC is shown in equation (39), where $F_s$ denotes the signal sampling frequency, N is the size of the data buffer, and $x_{norm}$ is a predetermined power value:

$$x_1 = \frac{1}{x_{norm}}\left(\frac{F_S}{N}\right)\sum_{n=1}^{N}[(y_{W,x}[n])^2 + (y_{W,y}[n])^2 + (y_{W,z}[n])^2] \quad (39)$$

The average arm angle predictor value ($x_3$) was determined using equation (40):

$$x_2 = \left(\frac{1}{N}\right)\sum_{n=1}^{N}\cos(\theta_{GW}[n]) \quad (40)$$

Note that, for this predictor value, it is unnecessary to explicitly determine the angle$_{GW}$ using an arccosine function, and the readily available cosine value calculated in equation (12) acts as a surrogate parameter indicating the mean arm angle. The predictor value indicating the standard deviation of the arm angle ($x_3$) was determined using equation (41) using the same assumptions for the angle $_{GW}$ as described above:

$$x_3 = \sqrt{\left(\frac{1}{N}\right)\sum_{n=1}^{N}(\cos(\theta_{GW}[n]) - x_2)^2} \quad (41)$$

The remaining predictor variables ($x_4$-$x_{10}$) are determined from the frequency content of the patient's motion, determined from the power spectrum of the time-dependent accelerometer signals, as indicated in FIG. 7. To simplify implementation of this methodology, it is typically only necessary to process a single channel of the ACC waveform. Typically, the single channel that is most affected by patient motion is $y_W$, which represents motion along the long axis of the patient's lower arm, determined from the accelerometer mounted directly in the wrist-worn transceiver. Determining the power requires taking an N-point Fast Fourier Transform (FFT) of the accelerometer data ($X_W[m]$); a sample FFT data point is indicated by equation (42):

$$X_W[m] = a_m + ib_m \quad (42)$$

Once the FFT is determined from the entire time-domain ACC waveform, the fractional power in the designated frequency band is given by equation (43), which is based on Parseval's theorem. The term mStart refers to the FFT coefficient index at the start of the frequency band of interest, and the term mEnd refers to the FFT coefficient index at the end of the frequency band of interest:

$$x_k = \left(\frac{1}{P_T}\right)\sum_{m=mStart}^{mEnd}(a_m + ib_m)(a_m - ib_m) \quad (43)$$

Finally, the formula for the total signal power, $P_T$, is given in equation (44):

$$P_T = \sum_{m=0}^{N/2}(a_m + ib_m)(a_m - ib_m) \quad (44)$$

As described above, to accurately estimate a patient's activity level, predictor values $x_1$-$x_{10}$ defined above are measured from a variety of subjects selected from a range of demographic criteria (e.g., age, gender, height, weight), and then processed using predetermined regression coefficients ($b_j$) to calculate a logit variable (defined in equation (37)) and the corresponding probability outcome (defined in equation (36)). A threshold value is then determined empirically from an ROC curve. The classification is declared true if the model output is greater than or equal to the threshold value. During an actual measurement, an accelerometer signal is measured and then processed as described above to determine the predictor values. These parameters are used to determine the logit and corresponding probability, which is then compared to a threshold value to estimate the patient's activity level.

Figure 19A:
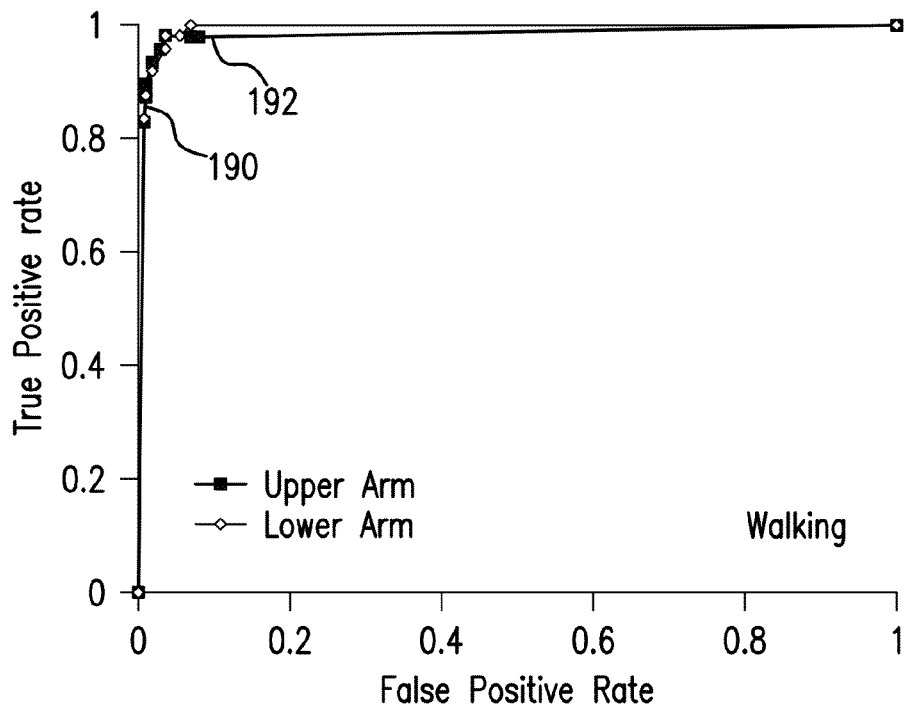
FIGS. 19A and 19B are receiver operating characteristic (ROC) curves characterizing, respectively, a patient that is walking and resting.

FIGS. 19A,B show actual ROC curves, determined using accelerometers placed on the upper and lower arms of a collection of patients. An ideal ROC curve indicates a high true positive rate (shown on the y-axis) and a low false positive rate (shown on the x-axis), and thus has a shape closely representing a 90 deg. angle. From such a curve a relatively high threshold can be easily determined and used as described above to determine a patient's activity level. Ultimately this results in a measurement that yields a high percentage of 'true positives', and a low percentage of 'false positives'. FIG. 19A shows, for example, a ROC curve generated from the patients' upper 192 and lower 190 arms during walking. Data points on the curves 190, 192 were generated with accelerometers and processed with algorithms as described above. The distribution of these data indicates that this approach yields a high selectivity for determining whether or not a patient is walking.

Figure 19B:
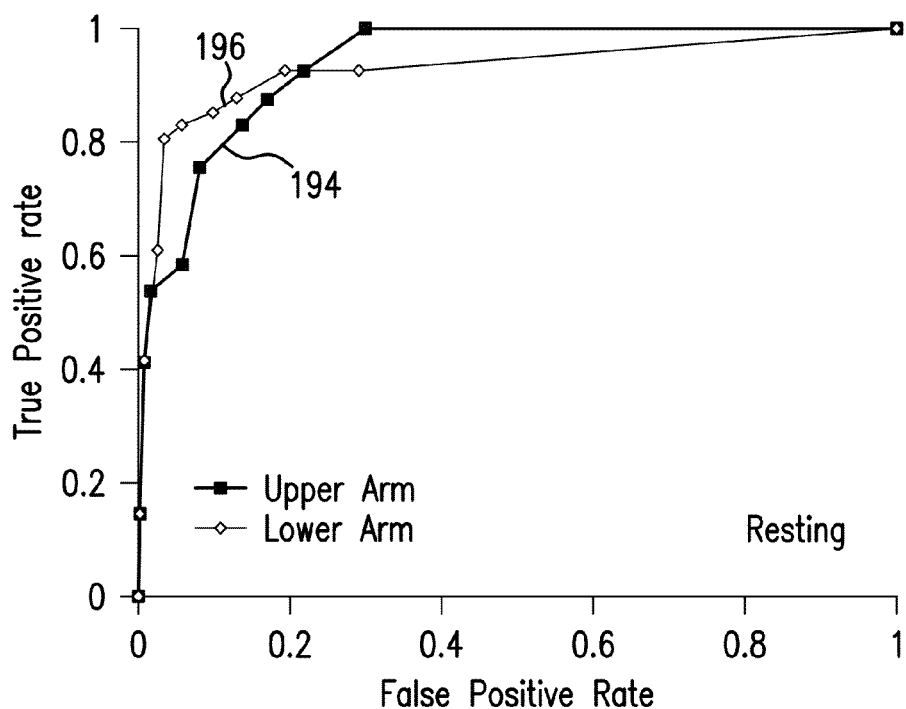

FIG. 19B shows data measured during resting. The ACC waveforms measured for this activity state feature fewer well-defined frequency components compared to those measured for FIG. 19A, mostly because the act of 'resting' is not as well defined as that of 'walking'. That is why the ROC curves measured from the upper 194 and lower 196 arms have less of an idealized shape. Still, from these data threshold values can be determined that can be used for future measurements to accurately characterize whether or not the patient is resting.

ROC curves similar to those shown in FIGS. 19A, B can be generated empirically from a set of patients undergoing a variety of different activity states. These states include, among others, falling, convulsing, running, eating, and undergoing a bowel movement. A threshold value for each activity state is determined once the ROC curve is generated, and going forward this information can be incorporated in an algorithm for estimating the patient's activity. Such an algorithm, e.g., can be uploaded wirelessly to the wrist-worn transceiver.

Hardware System for Body-Worn Monitor

FIGS. 20A and 20B show how the body-worn monitor 10 described above attaches to a patient 270. These figures show two configurations of the system: FIG. 20A shows the system used during the indexing portion of the composite technique, and includes a pneumatic, cuff-based system 285, while FIG. 20B shows the system used for subsequent cNIBP measurements. The indexing measurement typically takes about 60 seconds, and is typically performed once every 4 hours. Once the indexing measurement is complete the cuff-based system 285 is typically removed from the patient. The remainder of the time the system 10 performs the cNIBP measurement.

The body-worn monitor 10 features a wrist-worn transceiver 272, described in more detail in FIG. 21, featuring a touch panel interface 273 that displays blood pressure values and other vital signs. FIGS. 11A,B show examples of the touchpanel interface 273. A wrist strap 290 affixes the transceiver 272 to the patient's wrist like a conventional wristwatch. A cable 292 connects an optical sensor 294 that wraps around the base of the patient's thumb to the transceiver 272. During a measurement, the optical sensor 294 generates a time-dependent PPG which is processed along with an ECG to measure blood pressure.

PTT-based measurements made from the thumb yield excellent correlation to blood pressure measured with a femoral arterial line. This provides an accurate representation of blood pressure in the central regions of the patient's body.

To determine ACC waveforms the body-worn monitor 10 features three separate accelerometers located at different portions on the patient's arm. The first accelerometer is surface-mounted on a circuit board in the wrist-worn transceiver 272 and measures signals associated with movement of the patient's wrist. The second accelerometer is included in a small bulkhead portion 296 included along the span of the cable 286. During a measurement, a small piece of disposable tape, similar in size to a conventional bandaid, affixes the bulkhead portion 296 to the patient's arm. In this way the bulkhead portion 296 serves two purposes: 1) it measures a time-dependent ACC waveform from the mid-portion of the patient's arm, thereby allowing their posture and arm height to be determined as described in detail above; and 2) it secures the cable 286 to the patient's arm to increase comfort and performance of the body-worn monitor 10, particularly when the patient is ambulatory.

The cuff-based module 285 features a pneumatic system 276 that includes a pump, valve, pressure fittings, pressure sensor, analog-to-digital converter, microcontroller, and rechargeable battery. During an indexing measurement, it inflates a disposable cuff 284 and performs two measurements according to the composite technique: 1) it performs an inflation-based measurement of oscillometry to determine values for SYS, DIA, and MAP; and 2) it determines a patient-specific relationship between PTT and MAP. These measurements are performed according to the composite technique, and are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which have been previously incorporated herein by reference.

The cuff 284 within the cuff-based pneumatic system 285 is typically disposable and features an internal, airtight bladder that wraps around the patient's bicep to deliver a uniform pressure field. During the indexing measurement, pressure values are digitized by the internal analog-to-digital converter, and sent through a cable 286 according to the CAN protocol, along with SYS, DIA, and MAP blood pressures, to the wrist-worn transceiver 272 for processing as described above. Once the cuff-based measurement is complete, the cuff-based module 285 is removed from the patient's arm and the cable 286 is disconnected from the wrist-worn transceiver 272. cNIBP is then determined using PTT, as described in detail above.

To determine an ECG, the body-worn monitor 10 features a small-scale, three-lead ECG circuit integrated directly into a bulkhead 274 that terminates an ECG cable 282. The ECG circuit features an integrated circuit that collects electrical signals from three chest-worn ECG electrodes 278a-c connected through cables 280a-c. The ECG electrodes 278a-c are typically disposed in a conventional 'Einthoven's Triangle' configuration which is a triangle-like orientation of the electrodes 278a-c on the patient's chest that features three unique ECG vectors. From these electrical signals the ECG circuit determines up to three ECG waveforms, which are digitized using an analog-to-digital converter mounted proximal to the ECG circuit, and sent through a five-wire cable 282 to the wrist-worn transceiver 272 according to the CAN protocol. There, the ECG is processed with the PPG to determine the patient's blood pressure. Heart rate and respiratory rate are determined directly from the ECG waveform using known algorithms, such as those described in the following reference, the contents of which are incorporated herein by reference: 'ECG Beat Detection Using Filter Banks', Afonso et al., IEEE Trans. Biomed. Eng., 46:192-202 (1999). The cable bulkhead 274 also includes an accelerometer that measures motion associated with the patient's chest as described above.

There are several advantages of digitizing ECG and ACC waveforms prior to transmitting them through the cable 282. First, a single transmission line in the cable 282 can transmit multiple digital waveforms, each generated by different sensors. This includes multiple ECG waveforms (corresponding, e.g., to vectors associated with three, five, and twelve-lead ECG systems) from the ECG circuit mounted in the bulkhead 274, along with waveforms associated with the x, y, and z axes of accelerometers mounted in the bulkheads 275, 296. Limiting the transmission line to a single cable reduces the number of wires attached to the patient, thereby decreasing the weight and cable-related clutter of the body-worn monitor. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts.

More sophisticated ECG circuits can plug into the wrist-worn transceiver to replace the three-lead system shown in FIGS. 20A and 20B. These ECG circuits can include, e.g., five and twelve leads.

FIG. 21 shows a close-up view of the wrist-worn transceiver 272. As described above, it attaches to the patient's wrist using a flexible strap 290 which threads through two D-ring openings in a plastic housing 206. The transceiver 272 features a touchpanel display 200 that renders a GUI 273, similar to that shown in FIGS. 11A,B, which is altered depending on the viewer (typically the patient or a medical professional). Specifically, the transceiver 272 includes a small-scale infrared barcode scanner 202 that, during use, can scan a barcode worn on a badge of a medical professional. The barcode indicates to the transceiver's software that, for example, a nurse or doctor is viewing the user interface. In response, the GUI 273 displays vital sign data and other medical diagnostic information appropriate for medical professionals. Using this GUI 273, the nurse or doctor, for example, can view the vital sign information, set alarm parameters, and enter information about the patient (e.g. their demographic information, medication, or medical condition). The nurse can press a button on the GUI 273 indicating that these operations are complete. At this point, the display 200 renders an interface that is more appropriate to the patient, e.g. something similar to FIG. 11A that displays parameters similar to those from a conventional wristwatch, such as time of day and battery power.

As described above, the transceiver 272 features three CAN connectors 204a-c on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 204a-c, and means that these connectors are not associated with a specific cable. Any cable connecting to the transceiver can be plugged into any connector 204a-c. As shown in FIG. 20A, the first connector 204a receives the five-wire cable 282 that transports a digitized ECG waveform determined from the ECG circuit and electrodes, and digitized ACC waveforms measured by accelerometers in the cable bulkhead 274 and the bulkhead portion 296 associated with the ECG cable 282.

The second CAN connector 204b shown in FIG. 21 receives the cable 286 that connects to the pneumatic cuff-based system 285 used for the pressure-dependent indexing measurement. This connector receives a time-dependent pressure waveform delivered by the pneumatic system 285 to the patient's arm, along with values for SYS, DIA, and MAP values determined during the indexing measurement. The cable 286 unplugs from the connector 204b once the indexing measurement is complete, and is plugged back in after approximately four hours for another indexing measurement.

The final CAN connector 204c can be used for an ancillary device, e.g. a glucometer, infusion pump, body-worn insulin pump, ventilator, or end-tidal $CO_2$ delivery system. As described above, digital information generated by these systems will include a header that indicates their origin so that the CPU can process them accordingly.

The transceiver includes a speaker 201 that allows a medical professional to communicate with the patient using a voice over Internet protocol (VOIP). For example, using the speaker 101 the medical professional could query the patient from a central nursing station or mobile phone connected to a wireless, Internet-based network within the hospital. Or the medical professional could wear a separate transceiver similar to the shown in FIG. 21, and use this as a communication device. In this application, the transceiver 272 worn by the patient functions much like a conventional cellular telephone or 'walkie talkie': it can be used for voice communications with the medical professional and can additionally relay information describing the patient's vital signs and motion.

In addition to those methods described above, a number of additional methods can be used to calculate blood pressure from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No. _; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser.

No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other techniques, such as conventional oscillometry measured during deflation, can be used to determine SYS for the above-described algorithms.

Still other embodiments are within the scope of the following claims.

What is claimed is:

1. A system for continuously monitoring a plurality of patients, the system comprising:
 a plurality of patient monitors, each patient monitor configured to be worn on the body of one of the plurality of patients, each patient monitor comprising:
  a first sensor comprising a first detector configured to detect a first time-dependent physiological waveform indicative of one or more contractile properties of the patient's heart;
  a second sensor comprising a second detector configured to detect a second time-dependent physiological waveform indicative of one or more contractile properties of the patient's heart;
  at least two motion-detecting sensors positioned on locations selected from a forearm, upper arm, and a body location other than the forearm or upper arm of the patient, each of the motion-detecting sensors generating at least one motion waveform indicative of motion of a body location onto which the motion-detecting sensor is affixed;
  a location sensor comprising a wireless component and a location processing component, the location processing component configured to receive a signal from the wireless component and process this signal to determine a physical location of the patient to which the location sensor is attached;
  a processing component configured to receive the time-dependent physiological and motion waveforms and determine therefrom: (i) at least one vital sign calculated using at least one of the first and second time-dependent physiological waveforms; (ii) motion parameters corresponding to the patient's posture and activity state calculated using at least one motion waveform generated by each of the motion-detecting sensors; and (iii) an alarm parameter calculated from the at least one of the vital sign and motion parameters; and,
  a wireless transceiver configured to wirelessly transmit the vital sign, motion parameter, location of the patient, and alarm parameter through a wireless system; and,
 a remote computer system comprising a display and an interface to the wireless system,
  the interface configured to receive from the wireless system a vital sign, motion parameter, location of the patient, and motion-dependent alarm parameter corresponding to each of the plurality of patients, and
  the display configured to render a first user interface that, for each patient in the plurality of patients, displays (i) at least one vital sign, (ii) a graphical icon simultaneously indicating patient posture and activity state, (iii) a location of the patient, and (iv) motion-dependent alarm parameter, and to render a second user interface that displays a map corresponding to a monitored area of a hospital, the map depicting the current location of each patient in the plurality of patients within the monitored area of the hospital.

2. The system of claim 1, wherein the display is configured to render the motion-dependent alarm parameter as a graphical icon for each of the plurality of patients comprising a patient monitor.

3. The system of claim 1, wherein the patient monitor display is further configured to display the vital sign corresponding to the specific patient to which the patient monitor is attached, the motion parameter corresponding to the specific patient to which the patient monitor is attached, and the alarm parameter corresponding to the specific patient to which the patient monitor is attached.

4. The system of claim 1, wherein the wireless component comprised by the location sensor and the wireless transceiver are comprised by a common wireless system.

5. The system of claim 4, wherein the common wireless system operates a protocol based on 802.11.

6. The system of claim 4, wherein the common wireless system is comprised by a cellular network.

7. The system of claim 1, wherein the patient monitor configured to be worn on the body of each of the plurality of patients further comprises a first voice interface.

8. The system of claim 7, wherein the remote computer further comprises a second voice interface that integrates with the first voice interface.

9. The system of claim 1, wherein the wireless component comprised by the location sensor, the wireless transceiver, and the first and second voice interfaces are all comprised by a common wireless system.

10. The system of claim 9, wherein the common wireless system operates a protocol based on 802.11.

11. The system of claim 10, wherein the common wireless system is comprised by a cellular network.

12. The system of claim 1, wherein the remote computer system is comprised by a medical monitor, configured to be worn on the body of a person other than the patient.

13. The system of claim 1, wherein the patient monitor configured to be worn on the body of each of the plurality of patients further comprises a first voice interface.

14. The system of claim 13, wherein the medical monitor configured to be worn on the body of a person other than the patient further comprises a second voice interface that integrates with the first voice interface.

* * * * *